(12) United States Patent
Ranki et al.

(10) Patent No.: US 12,031,145 B2
(45) Date of Patent: Jul. 9, 2024

(54) CANCER THERAPY

(71) Applicant: Valo Therapeutics Oy, Helsinki (FI)

(72) Inventors: Tuuli Ranki, Helsinki (FI); Sari Pesonen, Helsinki (FI); Petri Priha, Helsinki (FI); Erkko Ylösmäki, Helsinki (FI); Vincenzo Cerullo, Helsinki (FI); Beatriz Martins, Helsinki (FI)

(73) Assignee: Valo Therapeutics OY, Helsinki (FI)

( * ) Notice: Subject to any disclaimer, the term of this patent is extended or adjusted under 35 U.S.C. 154(b) by 895 days.

(21) Appl. No.: 16/982,984

(22) PCT Filed: Mar. 19, 2019

(86) PCT No.: PCT/EP2019/056770
§ 371 (c)(1),
(2) Date: Sep. 21, 2020

(87) PCT Pub. No.: WO2019/179979
PCT Pub. Date: Sep. 26, 2019

(65) Prior Publication Data
US 2021/0332382 A1 Oct. 28, 2021

(30) Foreign Application Priority Data

Mar. 21, 2018 (GB) .................................. 1804468.5
Sep. 13, 2018 (GB) .................................. 1814866.8

(51) Int. Cl.
*C12N 15/86* (2006.01)
*A61P 35/00* (2006.01)
(Continued)

(52) U.S. Cl.
CPC .............. *C12N 15/86* (2013.01); *A61P 35/00* (2018.01); *C07K 16/2818* (2013.01);
(Continued)

(58) Field of Classification Search
CPC ...................... C12N 15/86; C12N 7/00; C12N 2710/10332; C12N 2710/10343;
(Continued)

(56) References Cited

U.S. PATENT DOCUMENTS

2008/0175871 A1 7/2008 Bradwell et al.

FOREIGN PATENT DOCUMENTS

WO WO 00/52045 9/2000
WO WO 2013/116778 8/2013
(Continued)

OTHER PUBLICATIONS

Francisco-Cruz A et al (Jan. 2014). "Granulocyte-macrophage colony-stimulating factor: not just another hematopoietic growth factor". Medical Oncology. 31 (1): 774. (Year: 2014).*
(Continued)

*Primary Examiner* — Jeremy C Flinders
*Assistant Examiner* — Thomas R. Amick
(74) *Attorney, Agent, or Firm* — Klarquist Sparkman, LLP

(57) ABSTRACT

The invention concerns a modified oncolytic adenovirus; a pharmaceutical composition comprising same; and a method of treating cancer using same.

20 Claims, 16 Drawing Sheets

Specification includes a Sequence Listing.

Adenovirus serotype 5
- Optimal for priming AND boosting T-cell responses
- Triggers primarily CD8+ T-cell responses: needed to kill tumor cells
- Pre-existing immunity against oncolytic virus enhances the efficacy of intratumoral treatment
- Good clinical safety record

Genetic Modifications
- chimera Ad5/3 capsid for increased tumor cell transduction
- D24 deletion in E1A for tumor-specific virus replication
- Partial deletion of E3 for increased immunogenicity
- Two co-stimulatory molecules as transgenes for the optimal activation of both innate and adaptive arms of the immune system:
  - Innate arm: CD40L for licensing APCs to drive CD8+ T-cell responses
  - Adaptive arm: OX40L for increased clonal expansion and survival of CD8+ T-cells and formation of larger pool of memory T-cells

(51) Int. Cl.
*C07K 16/28* (2006.01)
*C12N 7/00* (2006.01)

(52) U.S. Cl.
CPC ............ *C07K 16/2827* (2013.01); *C12N 7/00* (2013.01); *C12N 2710/10332* (2013.01); *C12N 2710/10343* (2013.01)

(58) Field of Classification Search
CPC . A61P 35/00; C07K 16/2818; C07K 16/2827; C07K 14/70575; C07K 14/70578; A61K 2039/6031; A61K 39/00; A61K 39/001186; A61K 39/001188; A61K 35/761; A61K 39/0011; A61K 45/06; A61K 2039/505; A61K 2039/525
See application file for complete search history.

(56) References Cited

FOREIGN PATENT DOCUMENTS

| WO | WO 2015/177098 | 11/2015 |
| WO | WO 2016/178167 | 11/2016 |

OTHER PUBLICATIONS

Diaconu, Iulia, et al. "Immune response is an important aspect of the antitumor effect produced by a CD40L-encoding oncolytic adenovirus." Cancer research 72.9 (2012): 2327-2338. (Year: 2012).*
"Evaluation of the humoral immune response against Cancer-Testis-Antigens after autologous and allogenic stem cell transplantation in patients with multiple myeloma," Dissertation of Eva Schlingloff, 2016, 94 pages (in German).
Miyai et al., "Detection and Tracking of NY-ESO-1-Specific CD8+ T Cells by High-Throughput T Cell Receptor β (TCRB) Gene Rearrangements Sequencing in a Peptide-Vaccinated Patient," *PLoS ONE*, vol. 10(8):e0136086, 2015 (15 pages).
Office Action from Russia Application No. 2020131336/10(056775), dated Feb. 20, 2023, and an English translation of the Office Action (12 pages).
Adams et al., "Immunization of Malignant Melanoma Patients with Full-Length NY-ESO-1 Protein Using TLR7 Agonist Imiquimod as Vaccine Adjuvant," *J. Immunol.*, vol. 181:776-784, 2008.
Capasso et al., "Oncolytic Adenoviruses Coated with MHC-1 Tumor Epitopes Increase the Antitumor Immunity and Efficacy against Melanoma," *OncoImmunology*, vol. 5:e1105429, 2016.
Capasso et al., "A Novel in silico Framework to Improve MHC-1 Epitopes and Break the Tolerance to Melanoma," *OncoImmunology*, vol. 6:e1319028, 2017.
Kakimi et al., "A Phase I Study of Vaccination with NY-ESO-1f Peptide Mixed with Picibanil OK-432 and Montanide ISA-51 in patients with Cancers Expressing the NY-ESO-1 Antigen," *Int. J. Cancer*, vol. 129:2836-2846, 2011.
Van Baren et al., "Tumoral and Immunologic Response after Vaccination of Melanoma Patients with an ALVAC Virus Encoding MAGE Antigens Recognized by T Cells," *J. Clin. Oncol.*, vol. 23:9008-9021, 2005.
Ylösmäki et al., "Abstract B123: Local Treatment with PeptiCRAd-1, a Novel Cancer Immunotherapy Approach, Mediates a Systemic Antitumour CD8+ T-cell Response and Infiltration of CD8+ and CD4+ T-cells into Distant Untreated Tumors in a Clinically Relevant Humanized Mouse Melanoma Model," Cancer Immunol. Res., vol. 7:Abstract No. B123, 2019.
International Search Report and Written Opinion from PCT/EP2019/056770, mailed Sep. 26, 2019, 19 pages.
International Preliminary Report on Patentability from PCT/EP2019/056770, mailed Feb. 20, 2020, 20 pages.
United Kingdom Intellectual Property Office search report from GB Application No. 1804468.5, dated Sep. 13, 2018, 4 pages.

* cited by examiner

NY-ESO-1 (aa91-110)

| | | HLA |
|---|---|---|
| KKKKKK | YLAMPFATPMEAELARRSLA | A24 |
| KKKKKK | YLAMPFATPMEAELARRSLA | B35 |
| KKKKKK | YLAMPFATPMEAELARRSLA | B52 |
| KKKKKK | YLAMPFATPMEAELARRSLA | C12 |
| KKKKKK | YLAMPFATPMEAELARRSLA | Cw3 |
| KKKKKK | YLAMPFATPMEAELARRSLA | B51 |

(6 to 9 lysine linker)

CLINICAL EVIDENCE

- Induces high frequency of CD8+ T-cells that are able to recognize natural epitopes on tumor cells (Eikawa Int J Cancer 2013).

- Elicites also CD4+ helper T-cell and humoral responses is cancer patients (Kakimi Int J Cancer 2011).

MAGE-A3 (aa161-180)

| | | HLA |
|---|---|---|
| KKKKKK | VFGIELMEVDPIGHLYIFAT | B18 |
| KKKKKK | VFGIELMEVDPIGHLYIFAT | B44 |
| KKKKKK | VFGIELMEVDPIGHLYIFAT | B35 |
| KKKKKK | VFGIELMEVDPIGHLYIFAT | A1 |
| KKKKKK | VFGIELMEVDPIGHLYIFAT | DR7 |

(6 to 9 lysine linker)

CLINICAL EVIDENCE

- Melanoma pts vaccinated with this peptide have been shown tumor regressions including complete responses (Marchand Int J Cancer 1999).

Figure 2

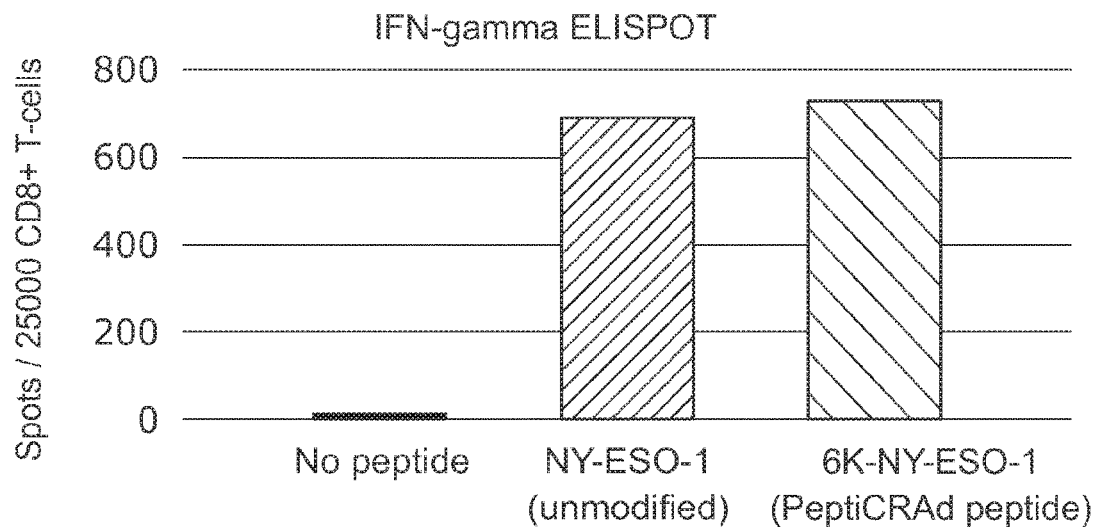
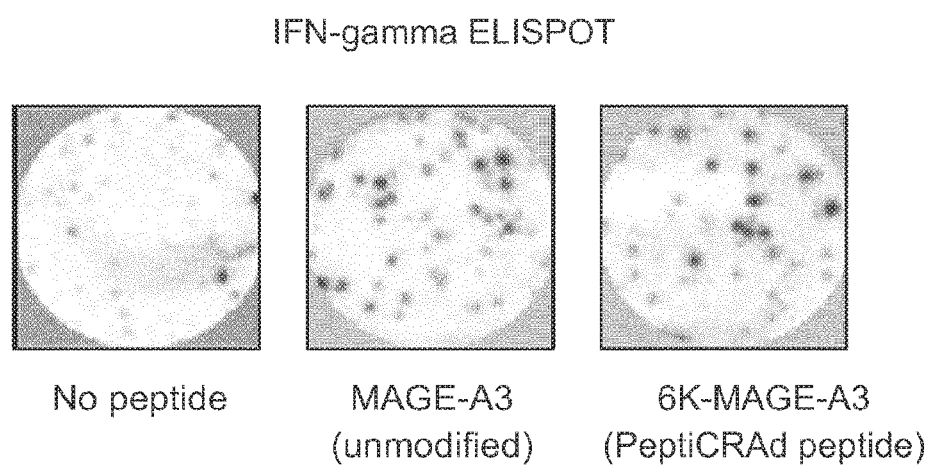
Figure 3

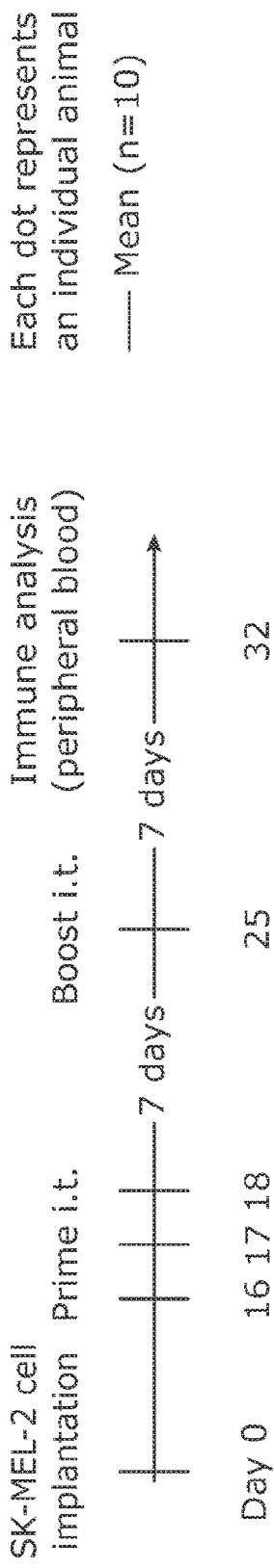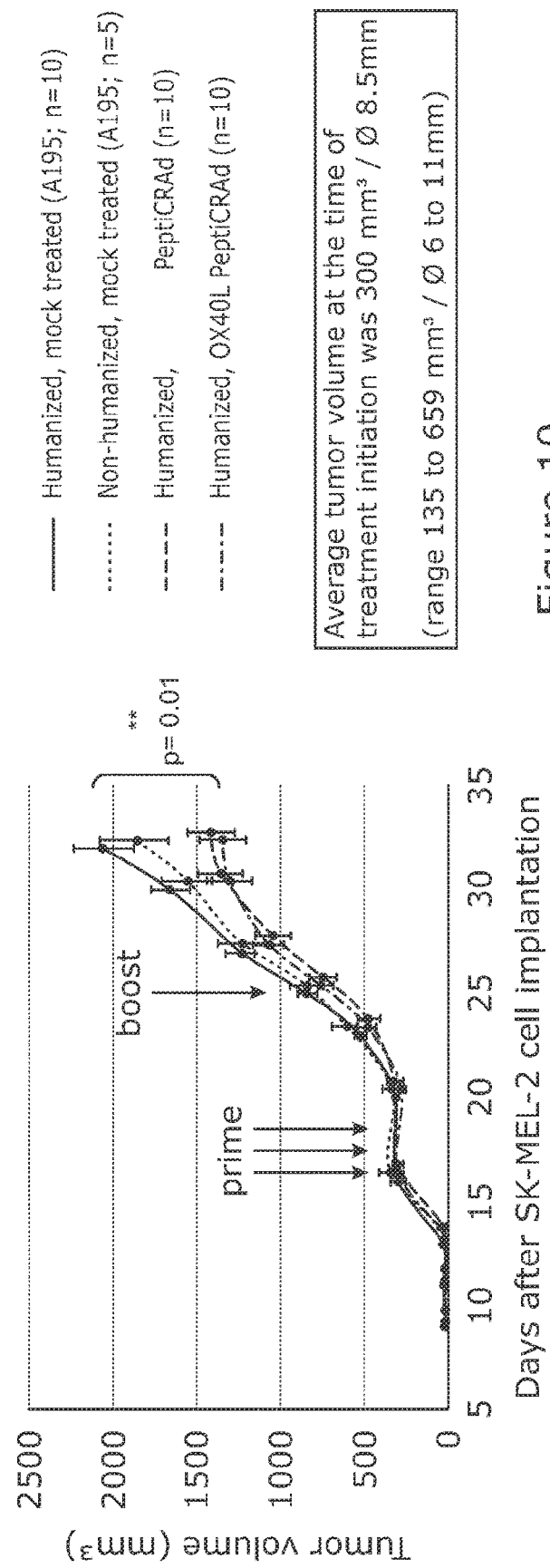
Figure 10

CANCER THERAPY

CROSS REFERENCE TO RELATED APPLICATIONS

This is the U.S. National Stage of International Application No. PCT/EP2019/056770, filed Mar. 19, 2019, which was published in English under PCT Article 21(2), which in turn claims the benefit of Great Britain Application No. 1814866.8, filed Sep. 13, 2018 and Great Britain Application No. 1804468.5, filed Mar. 21, 2018.

INCORPORATION OF ELECTRONIC SEQUENCE LISTING

The Sequence Listing is submitted as an ASCII text file, created on Sep. 17, 2020, 2.79 KB, which is incorporated by reference herein.

FIELD OF THE INVENTION

The invention concerns a modified oncolytic adenovirus; a pharmaceutical composition comprising same; and a method of treating cancer using same.

BACKGROUND OF THE INVENTION

The perception of the role of oncolytic viruses in cancer treatment has changed dramatically during the last decade, as immunotherapy and the stimulation of the patient's own immune system to target and attack cancer has gained popularity. At the beginning of the century, oncolytic viruses were perceived as active agents in cancer treatment, acting solely through their inherent ability to lyse tumor cells via oncolysis. Recently, their use as cancer vaccines has gained interest, and their ability to release tumor antigens from cancer cells upon oncolysis for activating the immune system is recognised as an important characteristic in designing the ultimate immunotherapy against cancer.

Adenoviruses are highly immunogenic viruses often used as vectors in various vaccine approaches against infectious diseases. Importantly, they have an exceptional ability to both prime and boost immune responses. Further, the presence of an oncolytic adenovirus within a tumor and the immunogenic cell death it causes is likely to shape the hostile tumor microenvironment towards a more susceptible state for a clinically relevant anti-tumor immunity to occur, by causing the expression of TH1-type immune modulators such as IFNgamma. However, the immunogenicity of oncolytic adenoviruses is a double-edged sword; the anti-virus immunity is often so overwhelming, that it overrides the much weaker immune response evoked against self-antigens expressed by the tumor.

Peptide vaccines have been an attractive concept in the immunotherapy of cancer, but the clinical efficacy of traditional peptide vaccine approaches is generally recognized as poor. Cancer vaccines deliver cancer antigens in combination with an adjuvant that should provide the necessary inflammatory signals for mounting an anti-tumor immune response. However, central and peripheral tolerance, as well as the process of immunoediting upon tumor progression, typically result in a loss of T-cell reactivity that is seen in vitro upon choosing the candidate peptides for peptide vaccines. The current vaccine adjuvants are simply not powerful enough to break tolerance in the immune suppressed tumor, even if the tumor expresses the chosen antigens. Further, many peptide vaccine approaches are based on short peptides that match the exact, minimal sequences of MHC class I-binding CD8+ T cell epitopes. Despite encouraging results in preclinical tumor models, short peptides have been shown to cause systemic peripheral tolerance in patients, which is postulated to result from the presentation of the peptides by non-professional APCs or non-matured DCs lacking the important co-stimulatory signals.

The current invention combines the above two vaccine approaches in a way that harnesses the best of both. A physical entity that combines an oncolytic adenovirus and cancer antigens resolves the problem of a) the overwhelmingly strong virus-specific target and the lack of an ample tumor-specific target for immune cells, b) the problem of a weak adjuvant and c) the problem of central tolerance evoked by short peptide vaccines. The invention thus concerns Peptide-coated Conditionally Replicating Adenovirus (PeptiCRAd) which is an innovative and unique way of combining two clinically proven cancer immunotherapy approaches: an oncolytic adenovirus and a peptide vaccine. PeptiCRAd uses immunogenic viruses as active carriers of tumor-specific peptides to direct the immune system to specifically target and kill cancer cells. Moreover, in contrast to oncolytic viral vaccines genetically coding tumor antigens, the coating of an adenovirus with an immunogenic peptide makes PeptiCRAd technology highly adaptive for all cancers; the same carrier virus can be used to treat all cancers and the adaptation occurs simply by coating the virus with different poly-lysine extended peptides. This unique technology utilizes the remarkable immunogenicity of the adenovirus and simultaneously directs the CD8+ T-cell response to tumor tissue.

STATEMENTS OF THE INVENTION

According to a first aspect of the invention there is provided a modified adenovirus or vector comprising:
at least one of the following polypeptides attached covalently or non-covalently onto the viral capsid without having been genetically encoded by said adenoviral vector
i) VFGIELMEVDPIGHLYIFAT [SEQ ID NO:1] MAGE-A3 161-180;
ii) YLAMPFATPMEAELARRSLA [SEQ ID NO:2] NY-ESO-1 91-110;
iii) RGPESRLLEFYLAMPFATPM [SEQ ID NO: 3] NY-ESO-1 81-100; or
iv) a polypeptide that is at least 60% identical therewith.

In a preferred embodiment of the invention said adenovirus is capable of replicating and having lytic activity in target cells.

Yet more preferably still said polypeptide of part iv) has 61, 62, 63, 64, 65, 66, 67, 68, 69 70, 71, 72, 73, 74, 75, 76, 77, 78, 79, 80, 81, 82, 83, 84, 85, 86, 87, 88, 89, 90, 91, 92 93, 94, 95, 96, 97, 98 or 99% identity with the polypeptide of parts 1) or ii) or iii).

Advantageously, said polypeptides can stimulate a peptide-specific immune response in a subject and, more advantageously still, because said polypeptides have not been genetically encoded by said adenoviral vector, but have been attached to the capsid covalently or non-covalently this attachment can be executed quickly and efficiently i.e. without having to wait for viral replication in a host cell to take place. Typically to facilitate attachment of at least one or two or three, polypeptides, said polypeptide(s) is/are poly-lysine extended using at least 4, ideally, 5, 6, 7, 8, or 9 lysines. Most typically 6 or 9 lysines are used and attached most preferably at the amino end of the polypeptide.

Accordingly, the peptides for attachment to the adenovirus are:

KKKK(KKKKK)-VFGIELMEVDPIGHLYIFAT [SEQ ID NO: 7]; and/or

KKKK(KKKKK)-YLAMPFATPMEAELARRSLA [SEQ ID NO: 8]; and/or,

KKKK(KKKKK)-RGPESRLLEFYLAMPFATPM [SEQ ID NO: 9]; alternatively:

KKKKKK-VFGIELMEVDPIGHLYIFAT [SEQ ID NO:4]; and/or

KKKKKK-YLAMPFATPMEAELARRSLA [SEQ ID NO:5]; and/or

KKKKKK-RGPESRLLEFYLAMPFATPM [SEQ ID NO:6].

In yet a further preferred embodiment of the invention said adenovirus may be of any type and species of adenoviridae e.g. not limited to human adenovirus but most typically is human adenovirus. Most favourably, the adenoviruses are capable of replicating and killing cancer cells while diverting the anti-viral immune response against the tumour, thus the modified adenovirus or vector is replication competent and oncolytic.

The adenovirus or vector used in the present invention can be made tumour specific with regard to replication, for example, the adenoviral vector may comprise modifications in E1, E3, E4 and/or L3 genes such as insertion of tumour specific promoters, gene deletions and the insertion of transgenes.

Ideally, the adenovirus or vector is oncolytic i.e. capable of infecting and killing cancer cells by selective replication in tumour versus normal cells.

The backbone of the adenovirus or vector may be of any serotype. In one embodiment of the invention the serotype of the adenovirus or vector backbone is selected from serotype 3 or 5. As used herein, "adenovirus serotype 5 (Ad5) nucleic acid backbone" refers to the genome of Ad5 and "adenovirus serotype 3 (Ad3) nucleic acid backbone" refers to the genome of Ad3.

Further, the virus or vector may be chimeric, e.g. Ad5/3, Ad3/5 or Ad5/35 vectors. As an example, "Ad5/3 vector" refers to a chimeric virus or vector having parts of both Ad5 and Ad3 vectors.

The "capsid" of the adenovirus or vector refers to the protein shell of the virus. The capsid consists of several oligomeric structural subunits made of proteins called protomers.

Most preferably, said adenovirus or vector is of serotype 5 which is selected because it is optimal for priming and boosting a T-cell response; it triggers the CD8+ T-cells needed to kill tumours; any pre-existing immunity against oncolytic viruses may enhance the efficacy of the intra-tumoral treatment and it has a good clinical safety record.

In yet a still further preferred embodiment of the invention said adenovirus or vector is further modified to include any one or more of the following features, including any and all combinations thereof.

An Ad5/3 chimeric substitution i.e. replacing the serotype 5 adenoviral fiber knob region with that of a serotype 3 adenovirus knob region; this allows the virus or vector to circumvent the Ad5 native receptor coxsackie-adenovirus receptor (CAR) and to use the Ad3 native receptor desmoglein 2 (DSG2) for internalisation instead. DSG2 is present abundantly in cancer cells.

Adenoviral infection commences with recognition of host cell receptors by means of specialised proteins on the viral surface i.e. the adenovirus fibre protein and in particular the globular carboxy-terminal domain of the adenovirus fibre protein, termed the carboxy-terminal knob domain. Accordingly, reference herein to a knob of an adenoviral fiber protein is reference to the globular carboxy-terminal domain of the adenovirus fibre protein.

A E1A gene deletion wherein the deletion is of nucleotides encoding amino acids 122-129 (LTCHEACF); this deletion is a safety measure as the viral or vector E1A protein cannot bind to a retinoblastoma (Rb) molecule and release the transcription factor E2F from Rb for viral gene transcription. Thus the adenovirus or vector relies on the presence of free E2F in a host cell and can replicate its genome in either dividing normal cells or in cancer cells, where free E2F is constantly available. Thus the modification is relatively protective of non-dividing cells and targeted against dividing or cancer cells.

Partial deletion of the E3 gene which, given the immunosuppressive role of this gene product, enhances immunogenicity. Ideally the 14.7K gene is partially or wholly deleted.

In a preferred embodiment said modified adenovirus or vector comprises the insertion of at least one transgene that encodes a co-stimulatory molecule and, ideally, two transgenes wherein one of said genes leads to activation of the innate immune system and the other leads to activation of the adaptive immune system. Preferred transgenes include CD40L for activating the innate immune system by the use of APCs to drive CD8+ T-cell responses and OX40L for activating the adaptive immune system by increasing clonal expansion, survival of CD8+ T-cells and the formation of a large pool of memory T-cells.

A number of transgenes may be placed in different positions of the adenovirus or vector. One transgene may be placed, for example, into a partially or totally deleted E3 region, either under the E3 promoter or under an exogenous promoter, or into a partially or totally deleted E1 region, either under the E1 promoter or under an exogenous promoter, or into a partially or wholly deleted L3 region under the L3 promoter or under an exogenous promoter.

Most preferably, OX40L, ideally human OX40L, is situated in the E3B region, replacing the gene 14.7K deletion.

Also most preferably, CD40L, ideally human CD40L is inserted in the late region of the virus, specifically in the late region 3 (L3), ideally, downstream from 23K gene.

In a preferred embodiment both transgenes are inserted into said virus i.e. OX40L and CD40L.

In the alternative DNA encoding OX40L and CD40L may be joined and inserted as a fusion molecule using known genetic engineering techniques, such as the use of an internal ribosomal entry site (IRES) or, more preferably, via the use of a self-cleaving 2A peptide which has the advantage of being a small size and having a high cleavage efficiency between genes upstream and downstream of the 2A peptide. Typically, CD40L is inserted immediately downstream from OX40L but it is possible to work the invention with the reverse configuration.

The virus or vector utilized in the present inventions may also comprise other modifications than described above. Any additional components or modifications may optionally be used but are not obligatory for the present invention.

It follows from the above that the adenovirus or vector of the invention has been engineered to stimulate an immune response against cancer and specifically in a tumour environment where, typically, the immune system is compromised by the evasive mechanisms employed by the cancer cells.

Surprisingly, our data indicates that the addition of the immunostimulatory transgenes, human OX40L and human CD40L, into the 14.7K locus does not compromise the oncolytic efficacy of the viruses of the present invention, when compared to the backbone virus Ad5/3D24 or a virus with an immunostimulatory transgene, e.g. human GM-CSF, replacing the deleted gp19K/7.1K genes. This is surprising because the transgenes may affect the virus replication profoundly due to the size of the transgene and the direct effects of the transgene on the cells that are infected. Additionally, the deletion of the 14.7K gene is not as extensively studied as the deletion of gp19K/7.1K genes and thus might have unexpected consequences for the replicative machinery of the virus, especially in the context of incorporating transgenes in the 14.7K deletion site.

We also show that the virus of the present application is able to produce functional human transgenes from the 14.7K gene locus. This was unexpected because we used, somewhat unusually, a transcription cassette with a viral 2A processing site in between the two transgenes.

Further, we show that the virus of the present invention is able to elicit a MAGE-A3 and NY-ESO-1-specific immune response.

Accordingly, the invention extends to a pharmaceutical composition comprising at least one modified adenovirus or vector of the invention and a suitable carrier. In a preferred embodiment of the invention said pharmaceutical composition is formulated for intratumoral, intramuscular, intraarterial, intravenous, intrapleural, intravesicular, intracavitary or peritoneal injection, or an oral administration.

Accordingly, in yet a further aspect the invention concerns a method of treating cancer in an individual comprising administering to the individual an effective amount of a pharmaceutical composition comprising at least one adenovirus or vector according to the invention.

Additionally, or alternatively still, the invention concerns at least one adenovirus or vector or composition according to the invention for use in treating cancer.

Additionally, or alternatively, the invention concerns the use of at least one adenovirus or vector or composition according to the invention to treat cancer.

Additionally, or alternatively, the invention concerns the use of at least one adenovirus or vector according to the invention in the manufacture of a medicament to treat cancer.

Given tumors have evolved several immunosuppressive mechanisms to counteract the immune cells of the body, the therapy of the invention is also practiced in combination with the use of a checkpoint molecule. The best characterized checkpoint pathways are cytotoxic T-lymphocyte protein 4 (CTLA-4) and programmed cell death protein 1 pathway (PD-1/PD-L1). Thus, the adenovirus or vector of the invention can be utilized in combination with checkpoint modulators such as anti-PD1, anti-PD-L1 or anti-CTLA-4 molecules to counteract immunosuppressive tumor environment and to cause a strong anti-immune response.

The modified adenovirus or vector acts as an active adjuvant because it provides the danger signals required for an optimal immune response against a target peptide, but also, in the case of a replicating adenovirus or vector, it retains its ability to lyse the cancer cells it infects and replicate its genome therein. The oncolytic cell killing is immunogenic by nature, which causes changes in the tumour micro-environment that are likely to strengthen the immune response to the peptides/tumour. Therefore, using our modified adenovirus: physically complexed with long (20 amino acid without the ploy-lysine tail) peptides results in a superior anti-tumor immune response when compared to either peptide vaccines or oncolytic vaccines alone.

Most preferably the cancer referred to herein includes any one or more of the following cancers: nasopharyngeal cancer, synovial cancer, hepatocellular cancer, renal cancer, cancer of connective tissues, melanoma, lung cancer, bowel cancer, colon cancer, rectal cancer, colorectal cancer, brain cancer, throat cancer, oral cancer, liver cancer, bone cancer, pancreatic cancer, choriocarcinoma, gastrinoma, pheochromocytoma, prolactinoma, T-cell leukemia/lymphoma, neuroma, von Hippel-Lindau disease, Zollinger-Ellison syndrome, adrenal cancer, anal cancer, bile duct cancer, bladder cancer, ureter cancer, oligodendroglioma, neuroblastoma, meningioma, spinal cord tumor, osteochondroma, chondrosarcoma, Ewing's sarcoma, cancer of unknown primary site, carcinoid, carcinoid of gastrointestinal tract, fibrosarcoma, breast cancer, Paget's disease, cervical cancer, cancer, esophagus cancer, gall bladder cancer, head cancer, eye cancer, neck cancer, kidney cancer, Wilms' tumor, liver cancer, Kaposi's sarcoma, prostate cancer, testicular cancer, Hodgkin's disease, non-Hodgkin's lymphoma, skin cancer, mesothelioma, multiple myeloma, ovarian cancer, endocrine pancreatic cancer, glucagonoma, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, acoustic neuroma, mycosis fungoides, insulinoma, carcinoid syndrome, somatostatinoma, gum cancer, heart cancer, lip cancer, meninges cancer, mouth cancer, nerve cancer, palate cancer, parotid gland cancer, peritoneum cancer, pharynx cancer, pleural cancer, salivary gland cancer, tongue cancer and tonsil cancer.

In the claims which follow and in the preceding description of the invention, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

All references, including any patent or patent application, cited in this specification are hereby incorporated by reference. No admission is made that any reference constitutes prior art.

Further, no admission is made that any of the prior art constitutes part of the common general knowledge in the art.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

Throughout the description and claims of this specification, the singular encompasses the plural unless the context otherwise requires. In particular, where the indefinite article is used, the specification is to be understood as contemplating plurality as well as singularity, unless the context requires otherwise.

An embodiment of the present invention will now be described by way of example only with reference to the following wherein:

FIG. 1 Shows a diagrammatic representation of a modified adenovirus in accordance with the invention. Specifically an Ad5 adenovirus is modified to include a serotype 3 knob protein i.e. Ad3 knob and, via the use of poly-lysine tails, at least one and ideally the two or three polypeptides of the invention are attached to the viral capsid, These polypeptides do not form part of the viral genome but are attached covalently or non-covalently to the capsid. Referred to herein as PeptiCRAd-1, this innovation thus harnesses all the major arms of the immune system, to attack cancer.

FIG. 2 Shows the two of the selected peptides. They do not bind to MHC class I molecules directly but require antigen processing by APCs to be presented. Therefore the peptides cannot bind to MHC class I molecules on nonprofessional APCs, and so do not cause transient activation and subsequent anergy of CD8+ T-cells. Only activated professional APCs (which can receive further co-stimulation from virus-coded CD40L where present in the further modified adenovirus) can present these peptides to T-cells leading to a robust activation and proliferation of peptide-specific CD8+ T-cells (further co-stimulation and enhanced memory T-cell response is provided from virus-coded OX40L where present in the further modified adenovirus).

FIG. 3 Shows a poly-lysine tail in the N-terminus of the peptides of FIG. 2 does not change the immunological properties of the peptides when compared to clinically used, unmodified peptides with known immune activation capability in cancer patients.

Figure 5A:
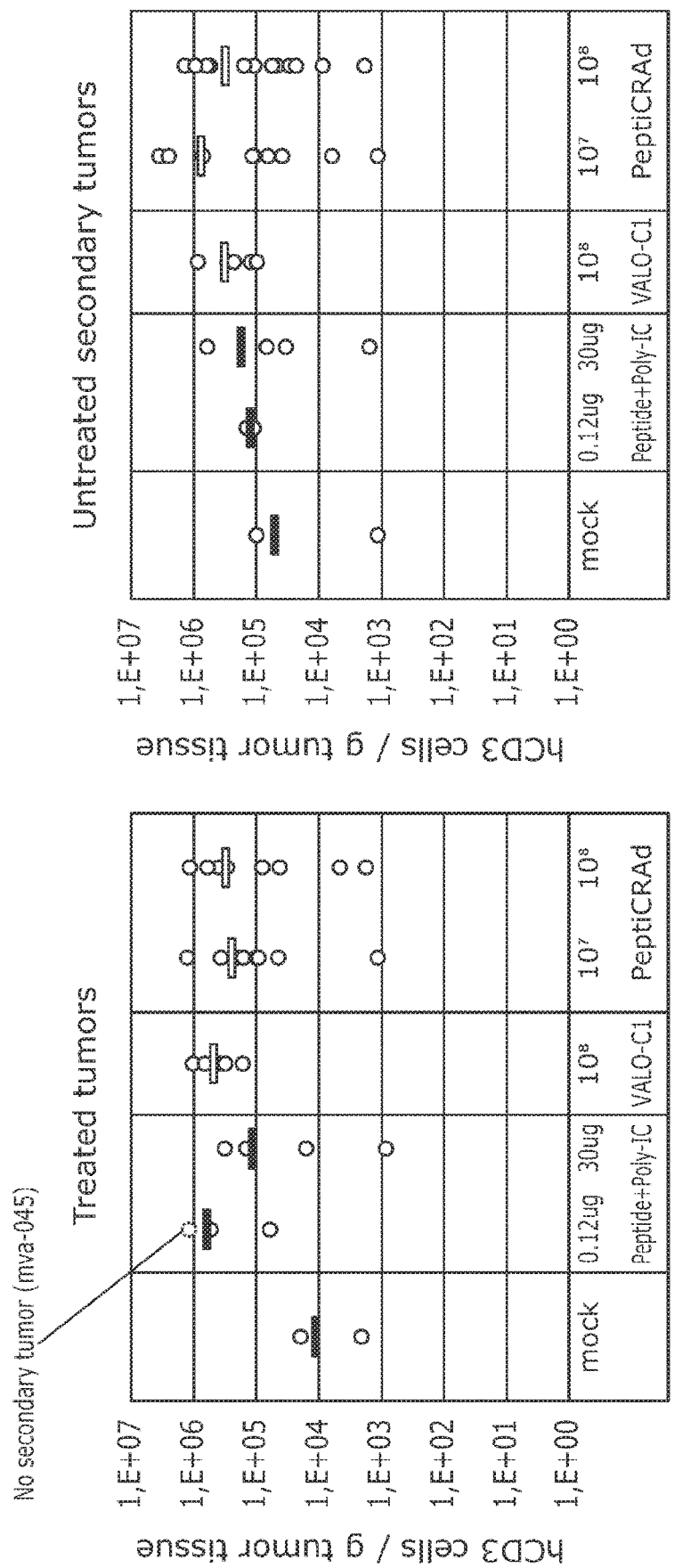
Figure 5B:
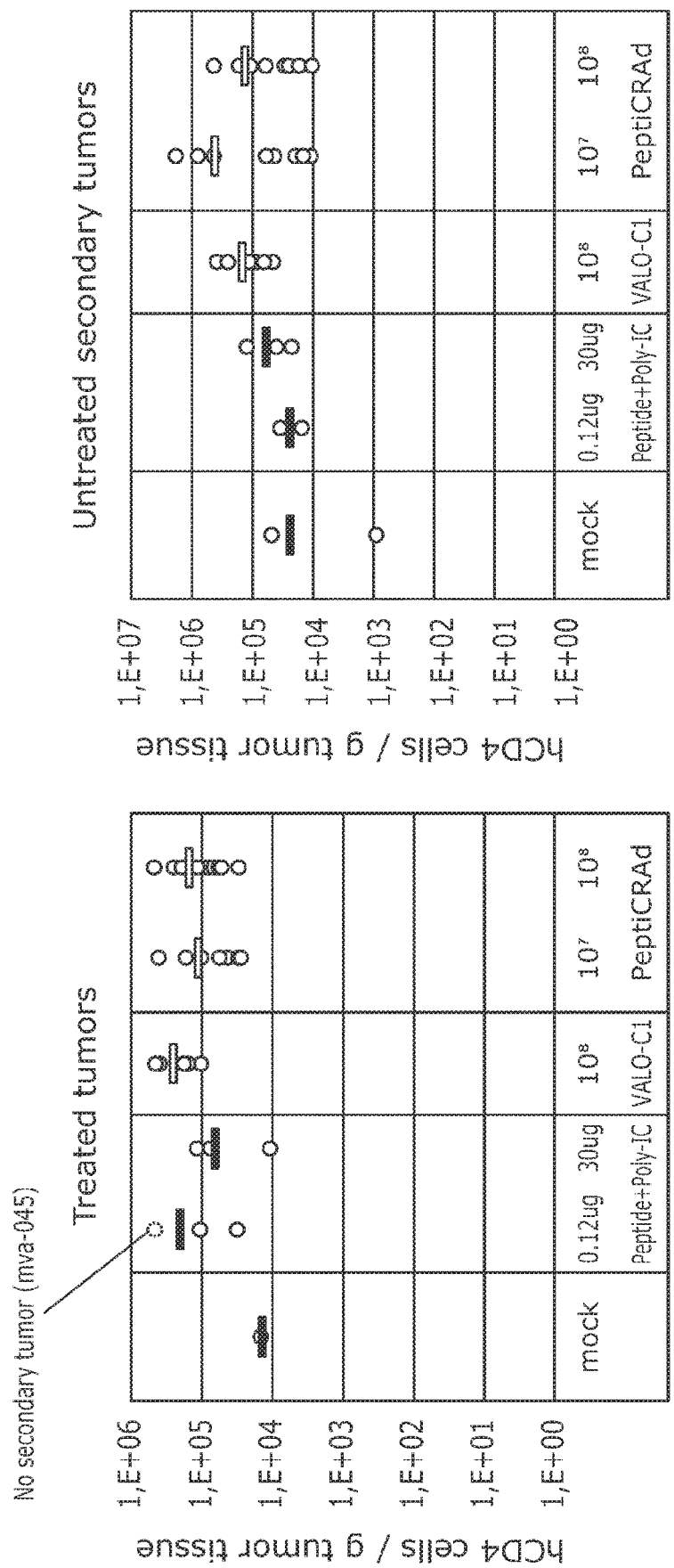
Figure 5C:
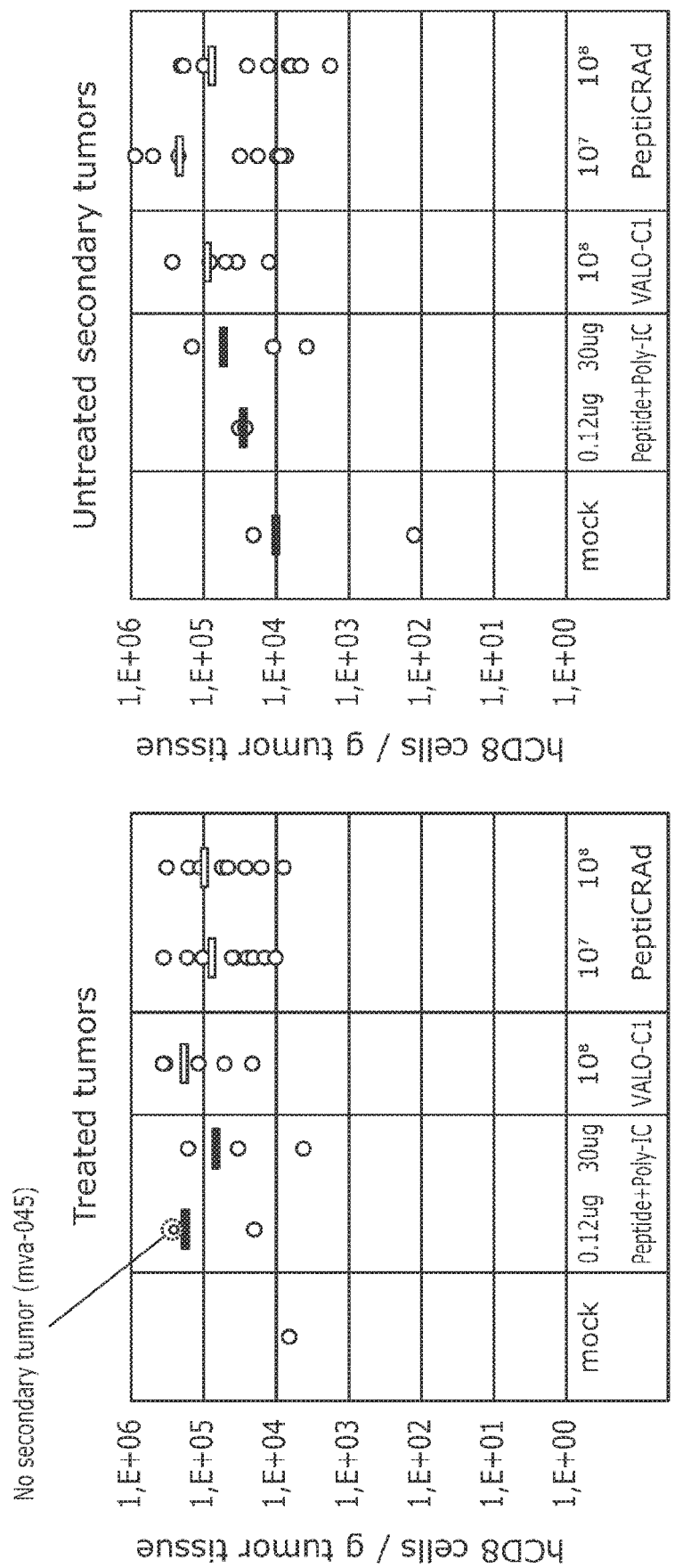

FIG. 5 shows the frequency of T cells in treated and contralateral, untreated tumor when treated with NYESO-1 and MAGE-A3-peptide coated modified virus according to the invention comprising a 5/3 capsid containing OX40L- and CD40L-expressing virus (PeptiCRAd-1) or the same virus without the NYESO-1 and MAGE-A3-peptide coating (VALO-C1) or peptide alone. The number of CD3+ T cells (A), CD4+ T cells (B) and CD8+ T cells (C) is depicted as cells per gram of tumor tissue in each treatment group. The treatments resulted in higher T cell frequencies in all groups compared to mock. The highest numbers were seen in tumors treated with VALO-C1 or PeptiCRAd.

Figure 6:
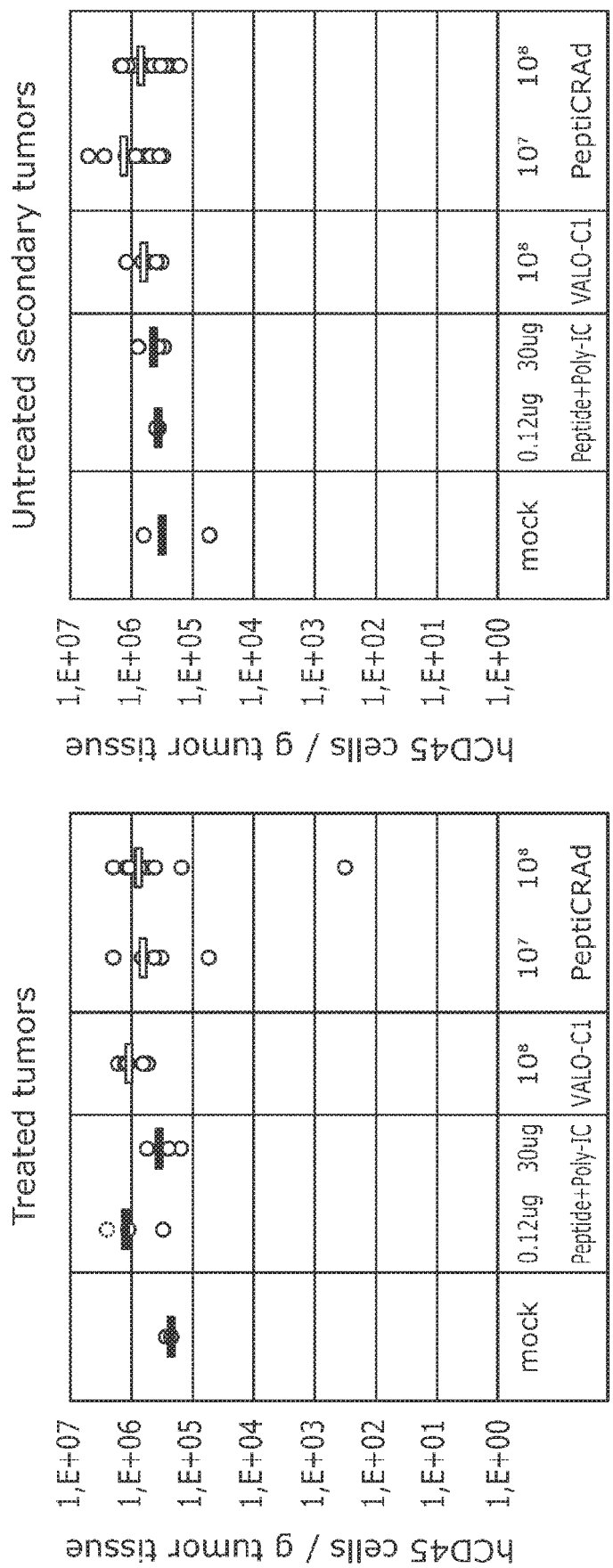

FIG. 6 shows the frequency of all immune cells (CD45+ cells) in treated and contralateral, untreated tumor when treated with PeptiCRAd-1 or the same virus without the peptide coating (VALO-C1) or peptide alone. The frequencies were similar in all groups with a somewhat lower number in mock treated animals.

Figure 7:
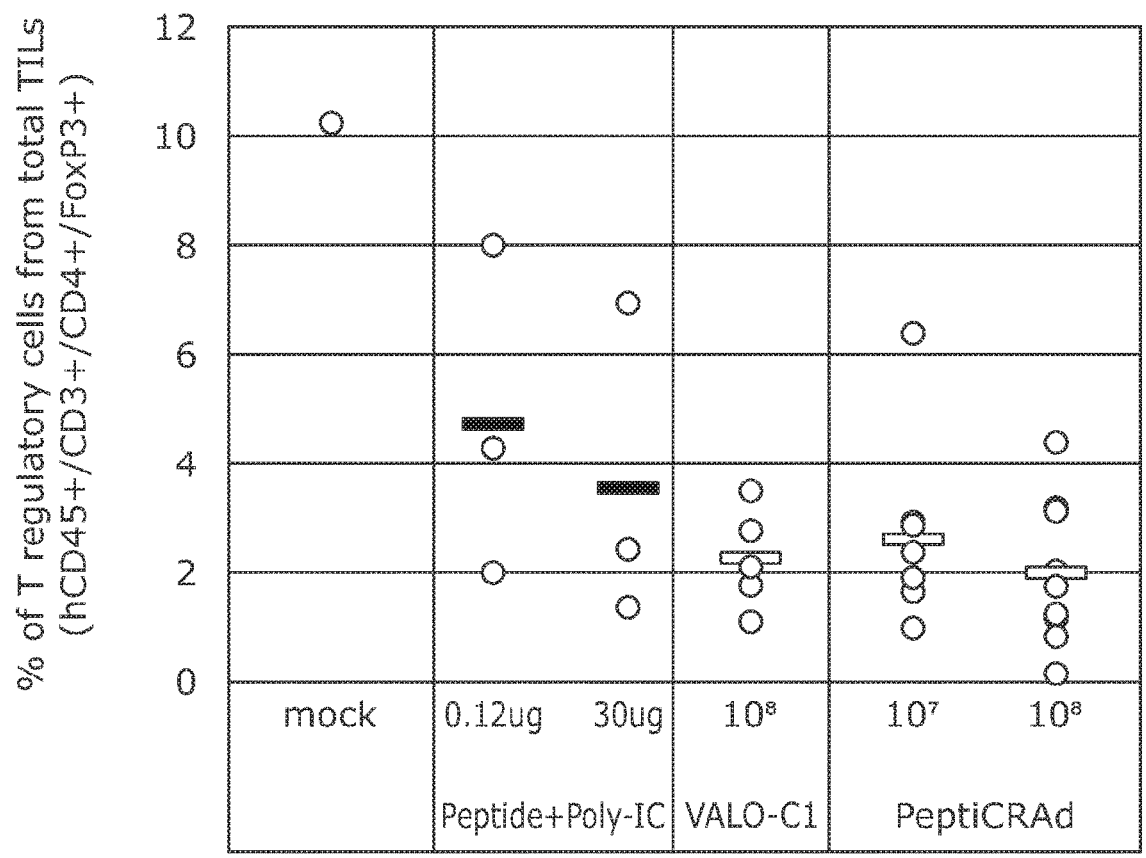

FIG. 7 shows the PeptiCRAd and VALO-C1-treatments decrease the percentage of regulatory T-cells from all TILs in treated tumors.

Figure 8A:
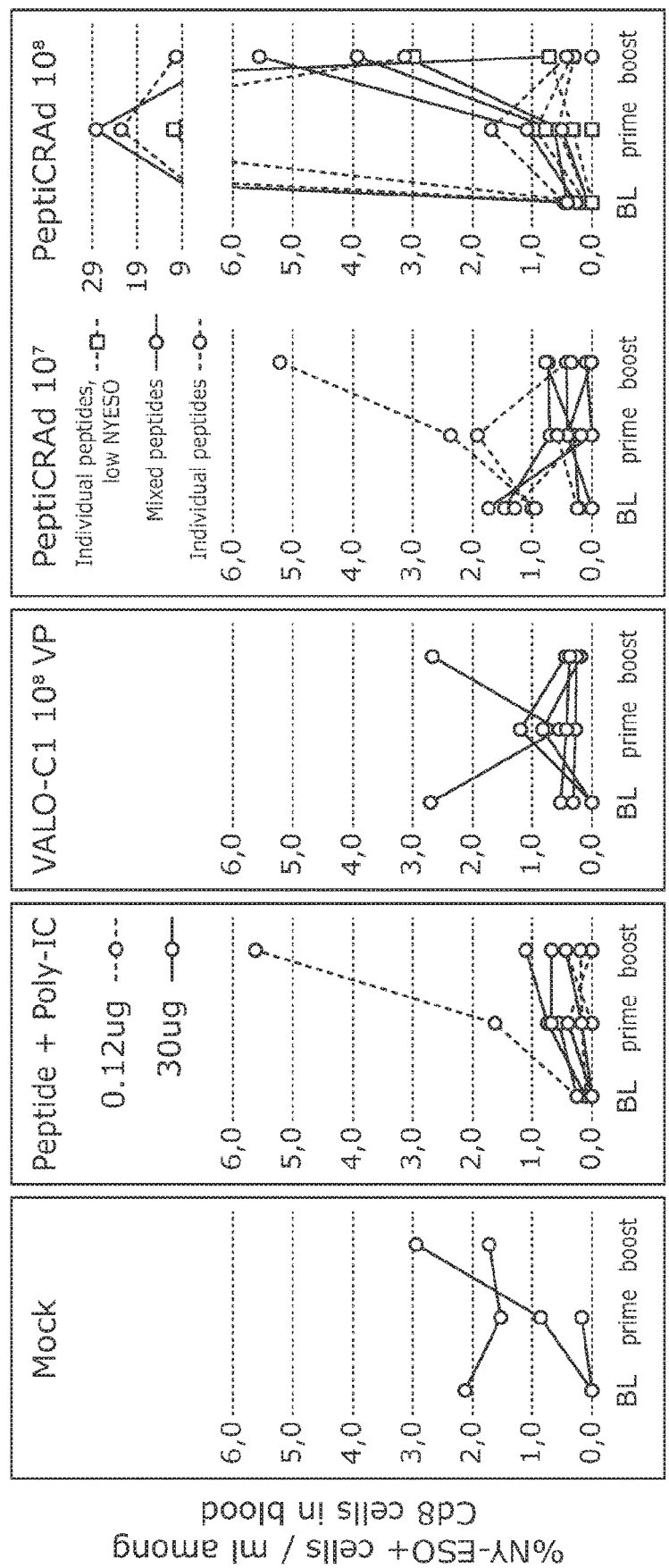
Figure 8B:
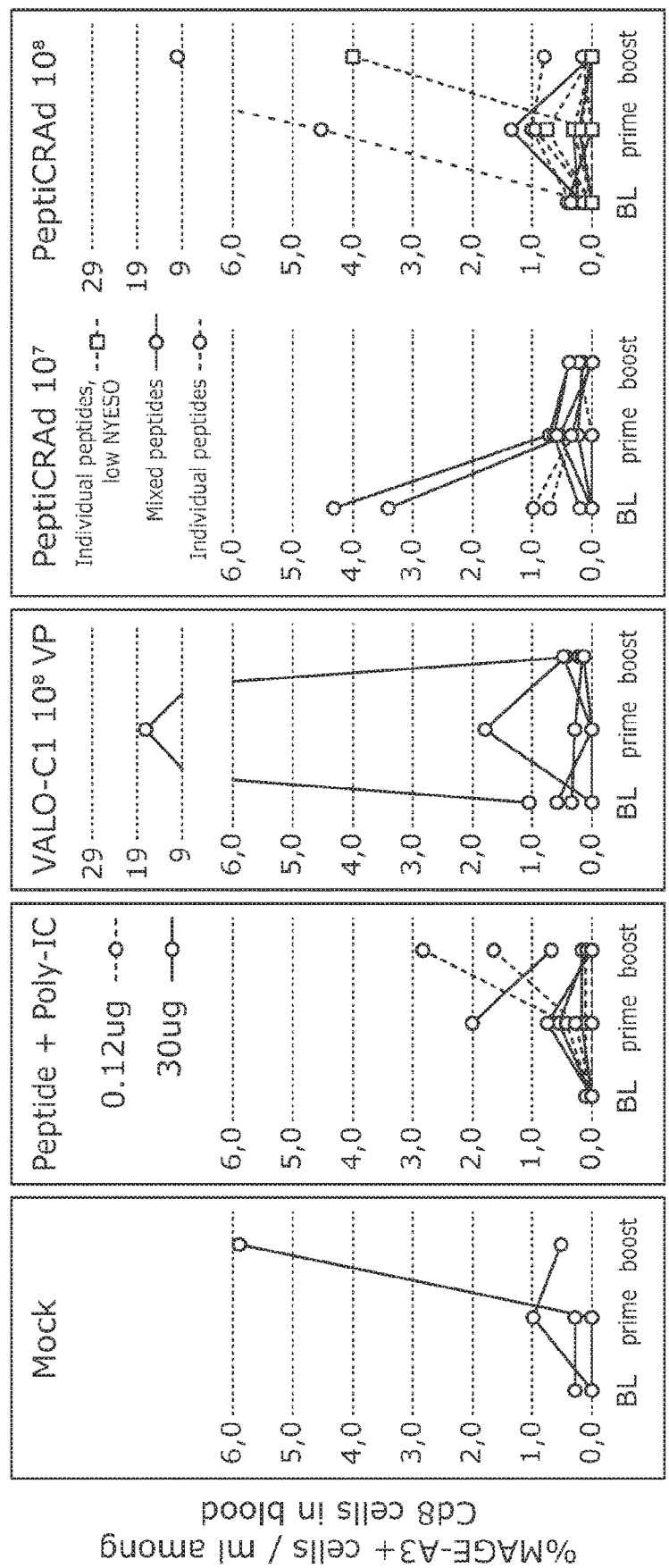

FIG. 8 shows the percentage of NY-ESO-1- (A) and MAGE-A3-specific (B) CD8+ T cells in blood tumor when treated with PeptiCRAd-1 or the same virus without the peptide coating (VALO-C1) or peptide alone. The percentage is calculated from all CD8+ T cells per 1 ml blood. The PeptiCRAd-treatment resulted in the highest percentage of NY-ESO-1-specific CD8+ T-cells, and both VALO-C1 and PeptiCRAd treatment resulted in higher percentage of MAGE-A3-specific when compared to either mock or peptide treated animals.

Figure 9:
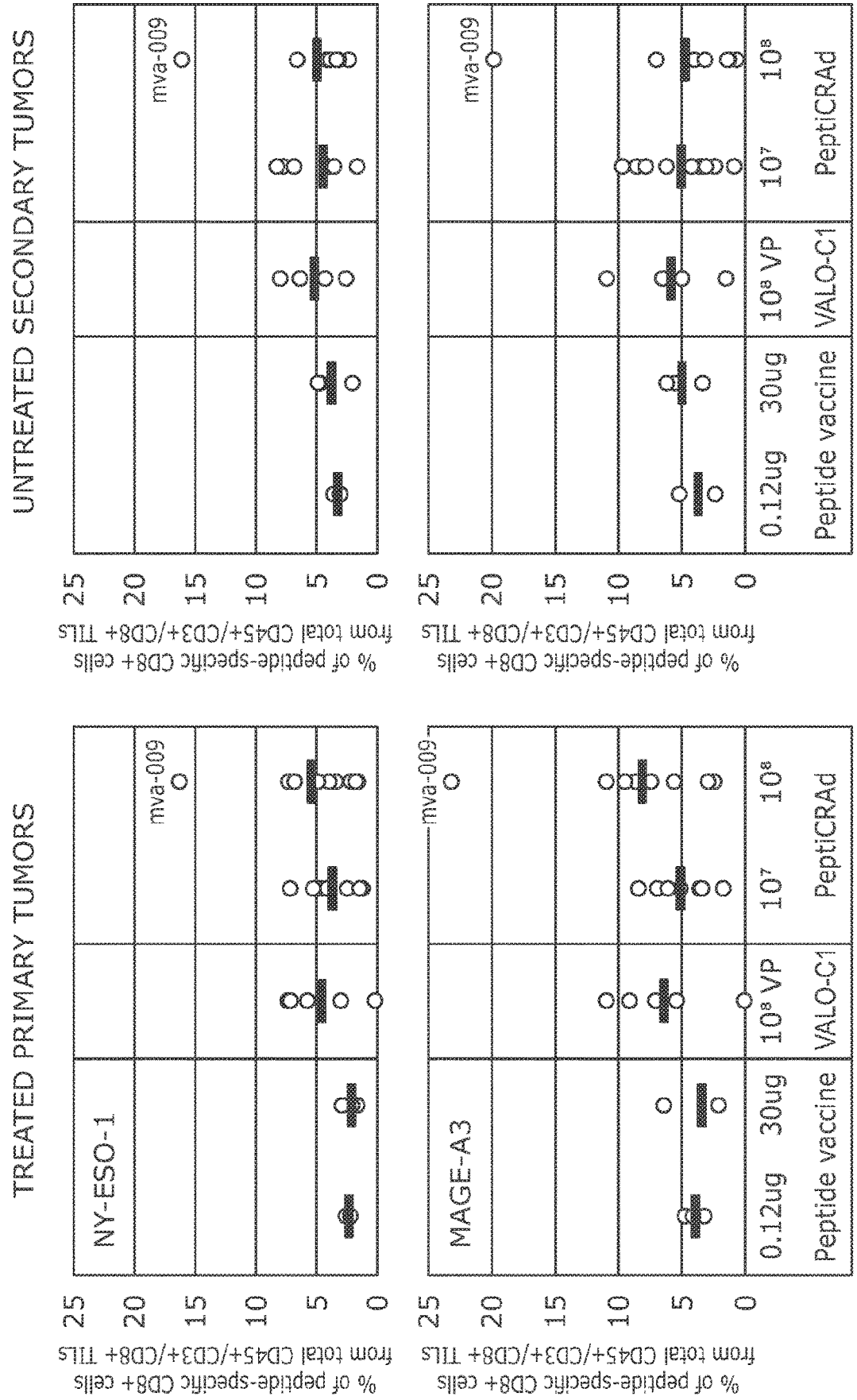

FIG. 9 shows the percentage of NY-ESO-1- or MAGE-A3-specific CD8+ T cells in treated or contralateral, untreated tumor when treated with PeptiCRAd-1 or the same virus without the peptide coating (VALO-C1) or peptide alone. The percentage is calculated from all CD8+ T cells per gram tumor tissue. VALO-C1 and PeptiCRAd are equally effective in recruiting peptide-specific CD8+ TILs to tumors.

FIG. 10 shows PeptiCRAd coated with NY-ESO-1 and MAGE-A3 proteins is able to stop tumor growth in humanized mouse melanoma model even if the treatment is started for large, well established tumors. Experimental design: $2\times10^6$ SK-MEL-2 cells were implanted subcutaneously (one tumor per animal) into flank of NOD/Shi-scid/IL-2Rγnull immunodeficient mice on day 1. On day 13, $5\times10^6$ PBMCs were injected intravenously. On day 16, $5\times10^4$ plasmacytoid and myeloid dendritic cells were injected intratumorally. Intratumoral PeptiCRAd treatments at a dose of $1\times10^9$ VP were given on days 16, 17, 18 (prime), and on day 25 (boost). First PeptiCRad dose was given immediately after DC injection. Tumor growth was followed. Animals were sacrificed on day 32. PeptiCRAd=Ad5/3-D24-OX40L-CD40L, an oncolytic adenovirus with 24 bp deletion in E1A, a 5/3 chimeric capsid and CD40L and OX40L transgenes expressed from the 14.7K locus, coated with NY-ESO-1 and MAGE-A3 peptides; OX40L PeptiCRAd=Ad5/3-D24-OX40L, an oncolytic adenovirus with 24 bp deletion in E1A, a 5/3 chimeric capsid and OX40L transgene expressed from the 14.7K locus, coated with NY-ESO-1 and MAGE-A3 peptides.

Figure 11:
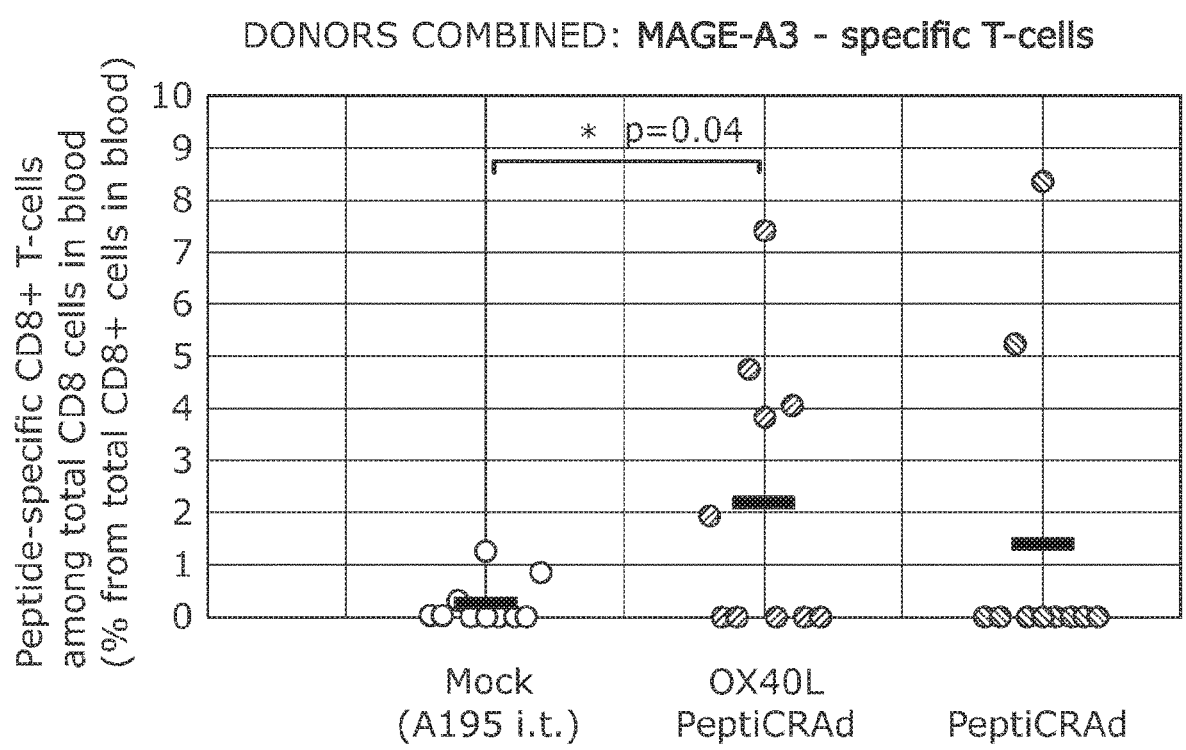

FIG. 11 shows OX40L-PeptiCRAd increased the number of MAGE-A3-specific CD8+ T-cells in peripheral blood in comparison to mock treated animals. Two animals treated with PeptiCRAd also showed increased number of MAGE-A3 specific CD8+ T-cells in blood. Anti-MAGE-A3 T-cells were assessed by flow cytometry (pentamer analysis) at the end of the previously mentioned tumor growth study on day 32.

Figure 12A:
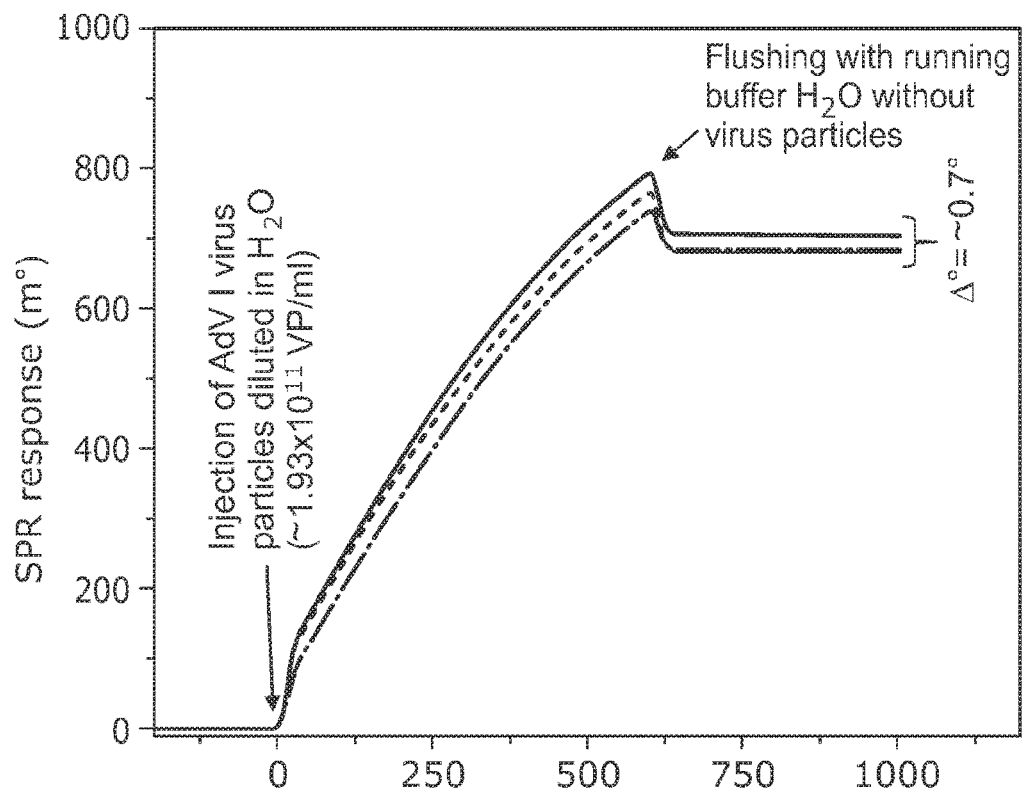

FIG. 12 A) Three separate SPR responses during AdV preparation diluted in sterile water and immobilization on APTES sensor using sterile water as the running buffer. $C=\sim1.93\times10^{11}$ VP/ml. B) SPR responses when 3 different peptide coatings: PEP1455=KKKKKK-VFGIELMEVDPIGHLYIFAT (SEQ ID NO: 4); PEP1456=KKKKKKKKK-VFGIELMEVDPIGHLYIFAT (SEQ ID NO: 7); PEP1508=KKKKKK-YLAMPFATPME-AELARRSLA (SEQ ID NO: 5). Stock solutions (5 mg/ml in sterile water) with increasing concentrations were allowed to interact with the immobilized AdV particles. Sterile water was used as the running buffer. Arrows indicate time points of peptide sample injection with corresponding concentration and stars indicate time point of start of flush with running buffer. $\Delta_{max}$ and $\Delta_{min}$ values marked in the figure corresponds to the SPR responses used to calculate number of peptides interacting per virus particle for each situation (peptide present in 100 μM in solution, $\Delta_{max}$, and no peptide in solution present, ($\Delta_{min}$)

Figure 13:
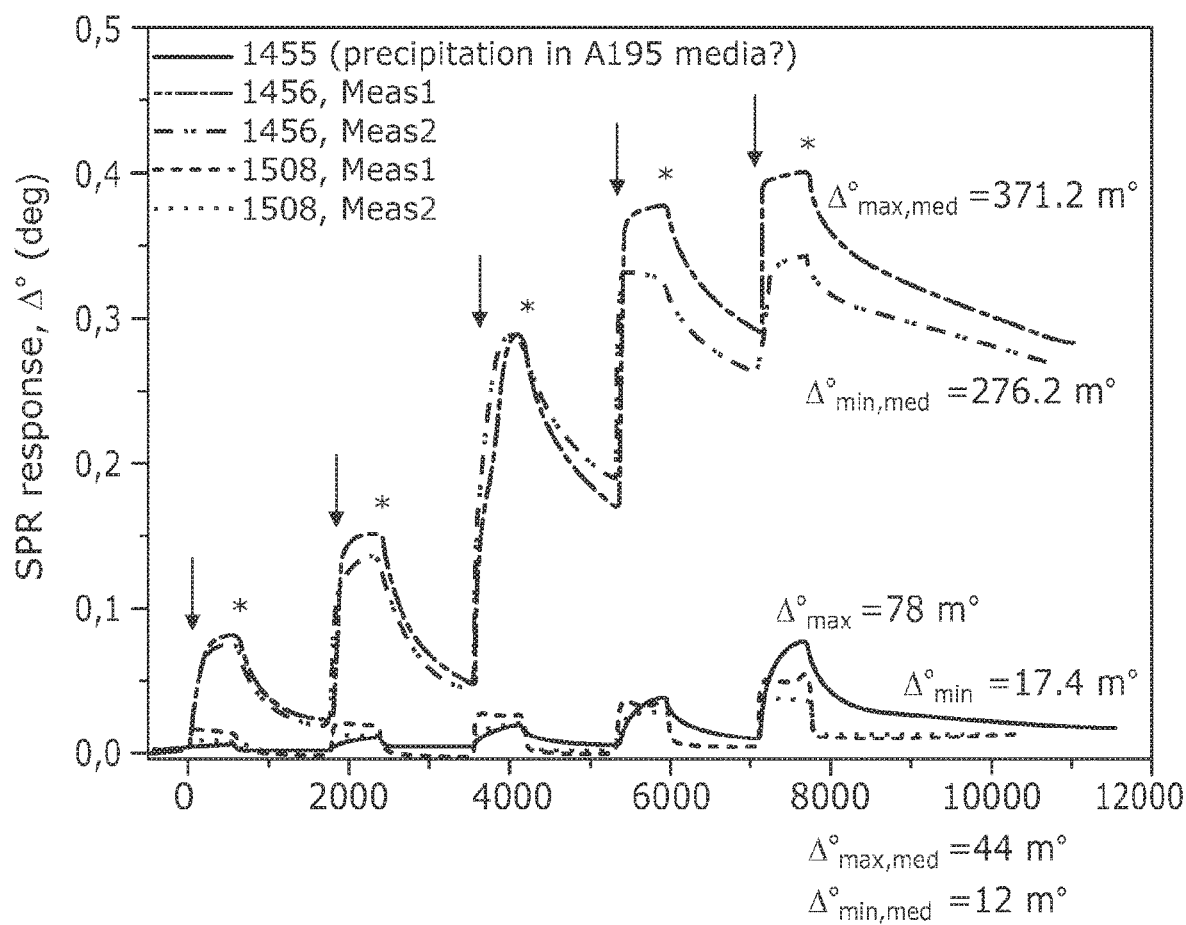

FIG. 13 SPR responses when increasing concentrations of peptide coatings PEP1455, PEP1456 and PEP1508 samples diluted in A195 buffer were allowed to interact with the immobilized AdV particles. Arrows indicate time point of peptide sample injection with corresponding concentration and stars indicate time point of start of flush with running buffer (A195 media). $\Delta_{max}$ and $\Delta_{min}$ values marked in the figure correspond to the SPR responses used to calculate number of peptides interacting per virus particle in each situation (peptide present in 100 μM in solution, $\Delta_{max}$, and no peptide in solution present, $\Delta_{min}$) The subscripts "min, med" and "max, med" refers to the median value of two separate measurements calculated from the corresponding measurements.

METHODS AND MATERIALS

Peptides:
Peptides were selected with acetate counter ion, which is a suitable salt form for human patients. The peptides were manufactured by PepScan.
The specific peptides intended for clinical use in PeptiCRAd are from:
MAGE-A3 protein (amino acids 161-180, sequence KKKKKK(KKK)-VFGIELMEVDPIGHLYIFAT)
20-mer peptides with either 6 (SEQ ID NO: 4) or 9 (SEQ ID NO: 7) lysine tail extending from the amino terminus
NY-ESO-1 protein (amino acids 91-110, sequence KKKKKK(KKK)-YLAMPFATPMEAELARRSLA)
20-mer peptide with 6 (SEQ ID NO: 5) or 9 (SEQ ID NO: 8) lysine tail extending from the amino terminus
NY-ESO-1 protein (amino acids 81-100, sequence KKKKKK(KKK)-RGPESRLLEFYLAMPFATPM)
20-mer peptide with 6 (SEQ ID NO: 6) or 9 (SEQ ID NO: 9) lysine tail extending from the amino terminus
Adenovirus Used in PeptiCRAd Preparations:
Adenovirus delta 24, serotype 5 virus with a modified knob from serotype 3 adenovirus (AdV 5/3). This model virus is not exactly the virus intended for clinical use, but it has an identical virus capsid. The difference between the model virus and the clinical virus is the clinical virus will ideally include genetic inserts coding for CD40L and OX40L, which have no contribution to the virus capsid and the attributes studied herein.
PeptiCRAd Complex Formation:
Individual peptides were diluted in water or 0.5% saline to reach a peptide stock concentration of 5 ug/μl. Virus stock in A195-buffer (1.45E+12 VP/ml) was diluted in water to reach a concentration of 1 E+9 VP/μl. Virus—peptide complex was prepared by mixing 1 or 3 μl of virus dilution (equating 1 E+9 or 3E+9 VPs) with variable volume of peptide(s) to reach a targeted peptide to virus ratio.
(PeptiCRAd, individual peptides); two individual aliquots of viruses were separately coated with single peptides. These two separate single peptide coated PeptiCRAds (NY-ESO-1 Complex and MAGE-A3 Complex) are then combined immediately before tumor injection. The separately coated viruses can also be given as separate injections Alternatively, NY-ESO-1 and MAGE-A3 peptides are first mixed together and this peptide mixture is then used for PeptiCRAd complex formation.
Zetasizer Measurements for the Complex Size and Charge:
The zetasizer measurements were performed immediately after complex formation, 15 minutes after mixing the components or after letting the complex stay still at room temperature (RT) approximately for 1.5 hours. The virus-peptide complexes were first diluted by adding 7000 of water to samples and then transferred to measurement cuvette. Hydrodynamic diameter (nm) was measured followed by measurement of zeta potential (mV). These parameters were measured three times and the average size and zeta potential were recorded.

Immunological Potency of PeptiCRAd-1 Peptides:
CD8+ T-cells from melanoma patients with known NY-ESO-1 and MAGE-A3 T-cell activities were pre-stimulated with unmodified peptides (SEQ ID NO: 2 NY-ESO-1 91-110: YLAMPFATPMEAELARRSLA or SEQ ID NO: 1 MAGE-A3 161-180: VFGIELMEVDPIGHLYIFAT). Recognition of poly-lysine extended peptides (SEQ ID NO: 5 NY-ESO-1 91-110: KKKKKKYLAMPFATPMEAELARRSLA or SEQ ID NO: 4 MAGE-A3 161-180: KKKKKKVFGIELMEVDPIGHLYIFAT) was studied by standard IFN-gamma ELISPOT method. The following ELISPOT protocol was used in the experiments: CD4+/CD8+ T-cells purified, with MACS® cell separation column (Miltenyi Biotech, Lund, Sweden), were pre-sensitized with peptide-pulsed (10 μg/ml) irradiated autologous PBMCs depleted of CD4+ and CD8+ T-cells (25000 cells/well). Pre-sensitized CD4+/CD8+ T-cells were tested on day 10-12 in IFNγ ELISPOT assay for recognition of peptide-pulsed (1 μg/ml) autologous antigen-presenting cells (EBV-transformed B cells or DCs). After 16 hours of incubation (37C.°) the number of cytokine-producing antigen-specific T-cells was evaluated using AID EliSpot Reader Classic ELR 07 (Autoimmun Diagnostika GmbH, Strassberg, Germany).
In Vivo Immunization
NOD/Shi-scid/IL-2Rγnull immunodeficient mice were humanized using hematopoietic stem cells (CD34+, HLA-B35+) isolated from human cord blood. A375 human melanoma tumors were implanted subcutaneously ($2 \times 10^6$ cells per 100 ul) and the animals were randomized into groups based on the humanization rate and the tumor size. The animals were treated either with PeptiCRAd-1 or the same virus without the peptide coating (VALO-C1) (virus dose $1 \times 10^8$ for both groups; a suboptimal dose of $1 \times 10^7$ was also tested for PeptiCRAd). Peptide vaccines (0.12 or 30 ug) were given intradermally with Poly-IC as an adjuvant.
The treatments started 25 days after randomization (DO) by a bolus dose of cyclophosphamide (1 mg/mouse i.v.). Treatments were given intratumorally (mock, virus and PeptiCRAd) or intradermally (peptide control) on days 1, 2, 3 and 12. Secondary tumors were implanted into the contralateral flank two days after the third treatment (day 5). No treatments for secondary tumors were given.
Peripheral blood mononuclear cells (PBMCs) and tumor infiltrating CD8+ lymphocytes (TILs) were analyzed for NY-ESO-1 YLAMPFATPMEAELARRSLA SEQ ID NO: 2 and MAGE-A3 VFGIELMEVDPIGHLYIFAT SEQ ID NO: 1 specific CD8+ T-cells by flow cytometry with dextramer analysis. Different immune cell subsets among PBMCs and TILs were assessed. The flow cytometric analysis was performed on Attune N×T Flow Cytometer (Life Technologies).
PBMC Mouse Model Immunization
35 eight-week old NOD-Prkdcem26Cd52/IL-2Ry em26Cd22/NjuCrl immunodeficient mice (NCG) were engrafted with $2 \cdot 10^6$ SKMEL-2 tumor cells (HLA-B35+) on the right flank (Day 0). On day 13, $5 \times 10^6$ HLA-B35+ human peripheral blood mononuclear cells (PBMC) from two different donors were injected intravenously. Intratumoral treatments with NYESO-1 (SEQ ID NO: 2) and MAGE-A3 (SEQ ID NO: 1)—complexed 5/3 capsid and containing OX40L-expressing virus ("OX40L PeptiCRAd") or a NYESO-1 (SEQ ID NO: 2) and MAGE-A3 (SEQ ID NO: 1)—complexed 5/3 capsid containing OX40L- and CD40L-expressing virus ("PeptiCRAd")—were initiated on Day 16 with a virus dose of $1 \times 10^9$ VP complexed with each peptide. Concomitantly with the first PeptiCRAd treatment, 50'000 autologous plasmacytoid and myeloid dendritic cells were injected intratumorally. On days 17, 18 (prime with the first treatment) and 25 (boost), the tumors were treated with intratumoral PeptiCRAd injections without addition of dendritic cells. The treatment schema is presented in FIG. 10. Tumor growth was followed. Animals were sacrificed on day 32. OX40L-PeptiCRAd and PeptiCRad contains a 24 bp deletion in E1A, a deleted gp19k/7.1K region, a human OX40L transgene expressed from the 14.7K locus and a 5/3 chimeric fiber.

Virus-Peptide Complexing

Immobilization of virus particles and interactions between peptide coatings and virus particles immobilized on APTES functionalized silica sensor surfaces were measured with a Multi-parametric Surface plasmon resonance (SPR) instrument equipped with a 2-channel polydimethylsiloxane (PDMS) flow channel and 96-well plate autosampler assembly (MP-SPR 220A). Peptide coatings were as follows PEP1455=KKKKKK-VFGIELMEVDPIGHLYIFAT (SEQ ID NO: 4); PEP1456=KKKKKKKKK-VFGIELMEVDPIGHLYIFAT (SEQ ID NO: 7); PEP1508=KKKKKK-YLAMPFATPMEAELARRSLA (SEQ ID NO: 5). The temperature, flow speed and laser wavelength used for all SPR measurements were +20° C., 20 µl/min and 680 nm, respectively.

For measurements in water, an adenovirus with a 5/3 chimeric fiber ($1.93 \times 10^{11}$ VP/a) diluted in sterile water was immobilized for 12 min on the APTES sensor, and triplicate measurements were done for each sample. Sterile water was used also as the running buffer. For measurements in A195 buffer, the adenovirus was first diluted in PBS and immobilized for 12 min on the APTES sensor. After the immobilization, PBS was replaced by A195 as the running buffer, and measurements were done as triplicates.

For measurements in sterile water, peptide stock solutions were prepared by dissolving 5 mg of peptide in 1 ml of water (5 mg/ml) resulting in corresponding concentrations of 1.65 mM for 6K-MAGE-A3 (PEP1455), 1.46 mM for 9K-MAGE-A3 (PEP1456) and 1.66 mM for 6K-NY-ESO (PEP1508). Peptide samples were injected sequentially in increasing concentrations for 6 minutes followed by an 8 min flushing period with the running buffer in between each sample concentration. Peptide concentrations used were 0.1, 0.3, 1, 3, 10, 30 and 100 µM.

For measurements in A195 buffer, peptide stock solutions were prepared by dissolving 340 µg of the corresponding peptides in A195 media to form 100 µM sample solutions, which were then used as a stock for preparing peptide sample solutions with lower concentrations. Peptide samples were injected sequentially in increasing concentrations for 10 minutes followed by a 15 min flushing period with the running buffer in between each sample concentration. Peptide concentrations used were 3.125, 6.25, 12.5, 25, 50 and 100 µM.

The calculations for estimating the number of peptides bound per viral particle were based on utilizing geometrical calculations of the estimated number of viral particles immobilized on the SPR sensor surface and the maximum number of peptides adsorbed determined by SPR measurements.

Results and Discussion

Effect of Net Charge of Peptide on Complex Formation

The MAGE-A3 peptide has a net charge of −3, 9 without a lysine tail. The three acidic amino acids rendering the negative charges are located close to the amino terminus (amino acids 5, 8 and 10). We investigated if the negative net charge of the peptide has to be compensated with a longer positive lysine tail (9 instead of 6 lysines) to achieve proper binding of peptides on the virus surface. Effect of lysine tail length on complex formation and stability of the complex was evaluated by determining zeta potential and average complex size of peptide coated virus samples containing 1 E+9 virus particles complexed with 20 or 40 µg of either peptide. The zetasizer measurements were performed immediately after complex formation, 15 minutes after mixing the components and after letting the complex stay still at room temperature (RT) approximately for 1.5 hours. Results are presented in table 1.

The size and zeta potential results show that complexes with MAGE-A3 peptide are formed regardless of length of the lysine tail suggesting that the negatively charged amino acids at least in the specific position of the peptide chain do not compromise complex formation. The longer lysine tail gave complexes with approximately 10% larger size and a bit lower zeta potential than corresponding peptide with the shorter lysine tail. Based on size of the complexes of freshly prepared samples and after keeping the samples for 1.5 hours at RT, complexes with either lysine tail were stable. In freshly prepared complexes the size was not affected by the amount of peptide used in complex formation but in samples kept for 1.5 h the results are a bit incoherent. In conclusion, it was decided to use six lysine tail peptides in subsequent zetasizer studies.

Effect of 6K-MAGE-A3-Peptide to Virus Ratio on Size and Zeta Potential of Complexes Peptide to virus particles ratios of 15, 30, 45 and 60 µg of peptide per 3E+9 virus particles were prepared to evaluate effect of ratio on the complex formation and stability (freshly prepared complexes vs. complexes kept at RT for 2 hours) based on determination of size and zeta potential of complexes.

The results in table 2 show a trend that the lower the peptide to virus ratio within the tested range the smaller the size of the complex, suggesting that an optimum ratio could be determined that results in peptide-virus complexes composed of single virus or composed of small aggregates formed of a couple of viruses. Complexes were also quite stable at least for two hours with zeta potential around +30 mV.

An attempt was made to determine the optimal peptide to virus ratio with 6K-MAGE-A3 peptide as indicated in table 3. The complex size results suggest that as low as 1-5 µg of 6K-MAGE-A3 peptide per 3E+9 virus particles equaling to a molar ratio range from 6.6E+4 to 3.3E+5 result in a stable complex. But with lower ratio the complexes tend to aggregate.

Effect of Virus Coating with 6K-MAGE-A3 Peptide on Infectivity

Ability of the complexed virus to infect tumor cells is one important aspect of the mechanism of action of PeptiCRAd. That is why the effect of peptide coating on virus infectivity was evaluated by preparing complexes with different peptide to virus ratios and by determining infectivity of the complex on A549 cells based on immunocytochemistry assay (ICC). The results in table 4 show that using a relevant peptide to virus ratio of approximately 1 µg, 62% of the infectivity of the virus only sample was retained, suggesting that virus coating does not affect infectivity dramatically.

Stability of 6K-MAGE-A3-PeptiCRAd at Different Temperatures

To evaluate stability of 6K-MAGE-A3-PeptiCRAd at different temperatures, complexes were prepared by mixing either 15 or 30 µg of 6K-MAGE-A3 peptide per 3E+9 VPs and by storing the samples at different conditions. Stability was tested by zetasizer from samples stored at RT, +5, −20, −80° C. for 18-20 hours. The results are presented in table 5. Average hydrodynamic diameter remained quite stable during the storage at different temperatures ranging from 165 nm to 276 nm suggesting that no considerable aggregation had occurred at any temperature tested. Zeta potential was above the level of +30 mV in every sample indicating good stability. The smallest particle size was attained after storage at −20° C. but also storage at +4° C. seemed to be favorable to prevent aggregation.

Effect of 6K-NY-ESO-1-Peptide (p81-100) to Virus Ratio on Size and Zeta Potential of Complexes Prepared in Water Another clinically interesting peptide, NY-ESO-1-peptide, was studied in terms of complex formation attributes, size and zeta potential, determined by zetasizer measurements. The results are presented in table 6 a. Regarding the size of the complex, this particular peptide seemed to follow a sine-wave like curve, starting from smaller complex size at small peptide to virus ratio following an increase in complex size as the ratio gets bigger reaching a local maximum at 1 μg of peptide after which the complex size starts to decrease until 60 μg where the complex size reaches a minimum of 180 nm. Regarding stability of the complex the zeta potential results suggest that a higher peptide to virus ratio is favorable as compared to 6K-MAGE-A3. The NY-ESO-1 peptide has a native charge of—1 having two negative and two positive amino acid close to amino terminus (the acidic ones in location 4 and 9 and the basic one in location 1 and 6 of the peptide sequence). Rest of the sequence of NY-ESO-1 is quite hydrophobic as also is the case with MAGE-A3-peptide.

Effect of 6K-NY-ESO-1-Peptide (p91-110) to Virus Ratio on Size and Zeta Potential of Complexes Prepared in Water 6K-NY-ESO-1-peptide (p91-110) was also studied in terms of complex formation attributes, size and zeta potential, determined by zetasizer measurements. The results are presented in table 6 b. Regarding the size of the complex, the peptide range from 0.5 to 1 μg results in only moderately aggregated complex, suggesting that the optimum ratio with this peptide resides somewhere between 1 and 5 μg per 3E+9 VPs. The corresponding zeta potential values remain close to zero suggesting that the stability of the complex might not be optimal with a tendency for aggregation.

The NY-ESO-1 peptide (p91-110) has a native charge of—1 having two negative and two positive amino acid close to carboxy terminus (the acidic ones in location 11 and 13 and the basic ones in location 16 and 17 of the peptide sequence). Rest of the sequence of NY-ESO-1 is quite hydrophobic. The location of positive charges close to C-terminus might enable also binding C-terminus to virus surface.

PeptiCRAd Coated with Both 6K-MAGE-A3- and 6K-NY-ESO-1 Peptides

Both clinically interesting peptides, NY-ESO-1- and MAGE-A3-peptide, were studied as mixtures in terms of complex formation attributes based on zetasizer measurements. The complexes were prepared both in water and in physiological NaCl (0.9%). The results are shown it table 7 a and b. The average size of the complex prepared by mixing equal amounts of each peptide with the virus was larger than average size of a complex prepared of 6K-MAGE-A3 peptide alone and smaller than size of a complex prepared of 6K-NY-ESO-1 peptide (p81-100) alone. The average size of less than 300 nm suggests that only moderate aggregation occurred during complex formation. The complex could be prepared both in water and in 0.9% NaCl with comparable complex sizes.

The average size of a complex prepared by mixing equal amounts of 6K-MAGE-A3 and 6K-NY-ESO-1 peptide (p91-110) with the virus was larger than average size of a complex prepared of 6K-MAGE-A3 and 6K-NY-ESO-1 peptide (p81-100). In water the average size difference of complexes was about 1.8-fold but was reduced to 1.3-fold in physiological NaCl. The average size of 400 500 nm suggests that only moderate aggregation occurred during complex formation.

Effect of NY-ESO-1-Peptide to Virus Ratio on Size and Zeta Potential of Complexes Prepared in Physiological NaCl Because the zetasizer size results of complexes formed with NY-ESO-1 peptide (p81 100) in water suggested a sine like behavior as a function of peptide concentration, we studied if the complex formation step in physiological salt solution would prevent possible non-specific interactions. Results are presented in table 8a. The results show that the complex size as a function of increasing peptide concentration followed a quite similar trend as the complex prepared in water. The complex size was larger but anyway quite consistent with peptide to virus ratio in range from 5 μg until 60 μg. The results suggest that an optimum peptide to virus ration could be found in range from 1 to 5 μg per 3E+9 VPs.

Figure 1:
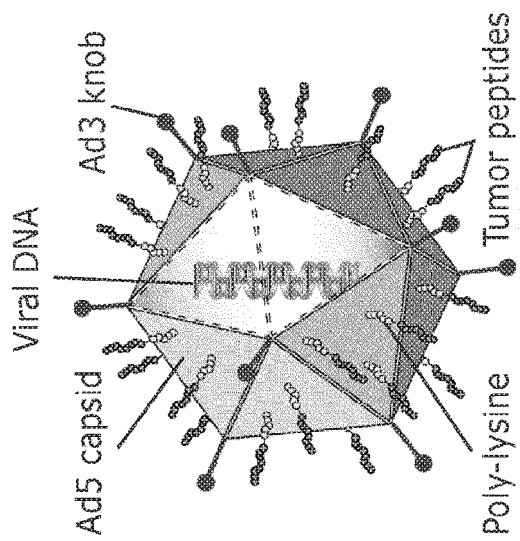
Figure 4:
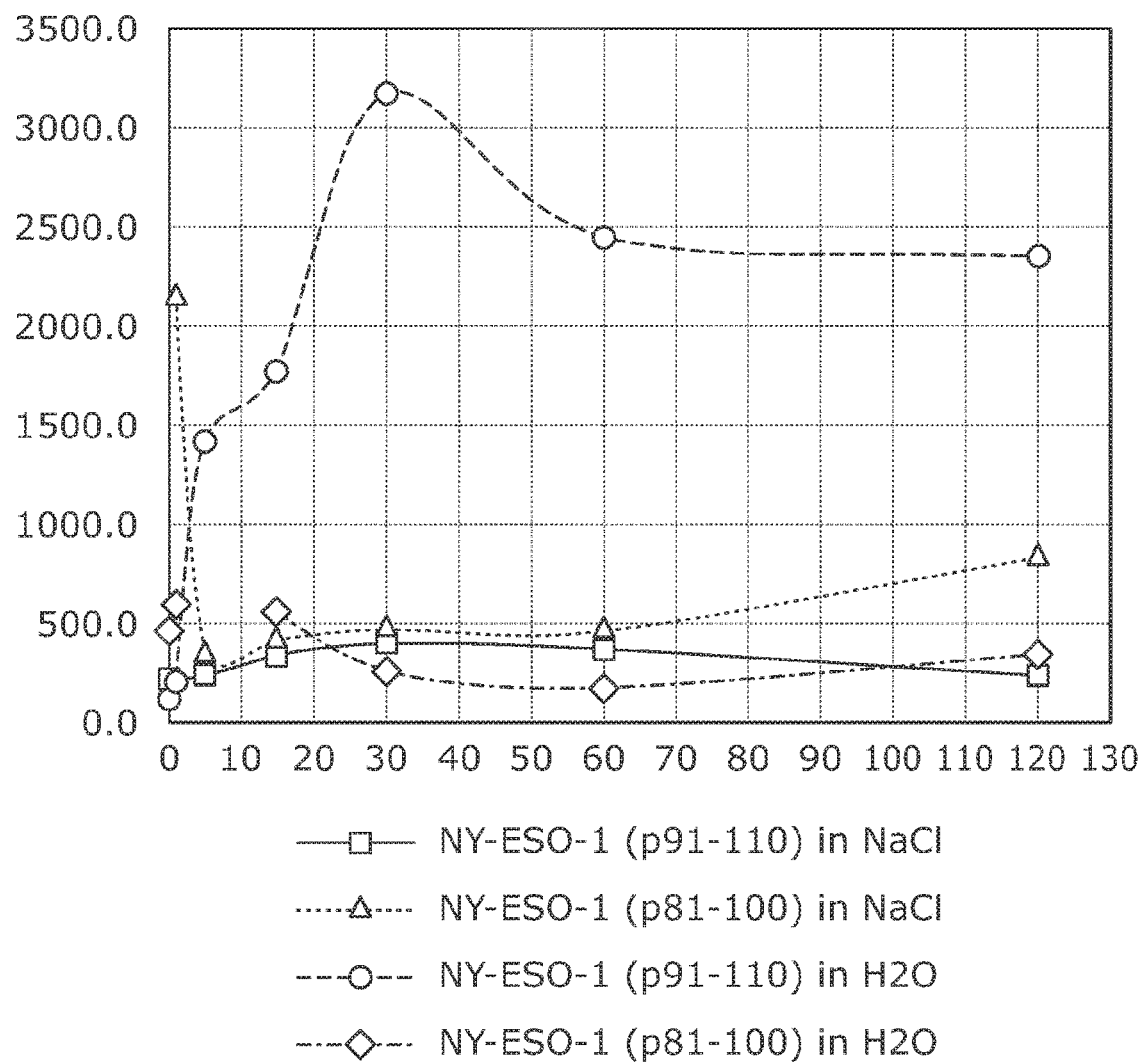
FIG. 4 Shows the average hydrodynamic diameter of both NY-ESO-1 peptide-virus complexes in water and physiological salt with different peptide concentrations.

The zetasizer average size results of complexes formed with NY-ESO-1 peptide (p91-110) in water suggested increasing aggregation with peptide to virus ratios higher that 1 μg, resulting in complex size larger than 3000 nm. We studied if the complex formation step in physiological salt solution would prevent aggregation. Results are presented in table 8 b and show that the complex size as a function of increasing peptide concentration was quite constant within a range of 200 400 nm. Thus, physiological NaCl in the liquid phase during complex formation could prevent aggregation quite dramatically as can be seen in FIG. 1 presenting data of both NY-ESO-1 peptide-virus complexes in water and physiological salt. With relevant peptide to virus ratios of 1-5 μg per 3E+9 VPs the complex size stayed within 217-245 nm.

Immunological Potency of PeptiCRAd-1 Peptides

Poly-lysine extended NY-ESO-1 and MAGE-A3 peptides trigger IFN-gamma production in cancer patient derived antigen-specific CD8+ T-cells upon in vitro stimulation as effectively as unmodified peptides (FIG. 3) indicating the poly-lysine modification does not affect function.

PeptiCRAd Elicits Peptide Specific Immune Response in a Humanized Mouse Model

All active treatments (peptide alone, virus without peptide coating [VALO-C1], and virus with NY-ESO-1 and MAGE-A3 peptide coating [PeptiCRAd]) increased the number of immune cells in primary tumors in comparison to mock treated animals. Both VALO-C1 and PeptiCRAd-1 treated animals showed more T-cells (CD3, CD4, CD8) in primary tumors in comparison to peptide vaccine or mock treated animals post treatment, while the number of overall infiltrating immune cells (CD45) was similar in all groups (FIGS. 5 and 6, respectively).

Furthermore, the number of T regulatory cells (CD3+/CD4+/FoxP3+) was smaller in VALO-C1 and PeptiCRAd-1 treated primary tumors in comparison to primary tumors from peptide vaccine or mock treated animals (FIG. 7). This suggests that intratumorally administered immunogenic adenovirus (either naked virus VALO-C1 or PeptiCRAd-1) modulates the tumor microenvironment by reducing local immune-suppression.

Unlike VALO-C1 treated animals, PeptiCRAd-1 treated animals showed more CD4+ and CD8+ T-cells in untreated secondary tumors than in treated primary tumors, suggesting that tumor-targeting via peptide-coating of the virus was critically important for the induction of an effect in distant untreated tumors (Table 9). Furthermore, PeptiCRAd-1 treated animals had more NYESO-specific CD8+ T-cells in blood post priming (mean=4.3% of total CD8+ cells) in comparison to OV treated (mean=0.6%) or peptide vaccine treated (mean=0.6%) animals (FIG. 8). The frequency of MAGE-specific CD8+ TILs in PeptiCRAd- and VALOC1-treated animals—in treated and untreated tumors—was higher than the frequency of MAGE-specific CD8+ T cells in peptide-treated animals (FIG. 9). Interestingly, higher frequency of MAGE-specific CD8+ T-cells was seen in VALOC1- and PeptiCRAd-treated tumors compared to NY-ESO-1-specific CD8+ T-cells, while the opposite was true in blood.

PeptiCRAd Elicits Peptide-Specific Immune Response in a PBMC Mouse Model

Treatments with NY-ESO-1- and MAGE-A3-complexed PeptiCRAd resulted in tumor growth arrest in humanized mouse melanoma model even when the treatment was started for large, well established tumors (FIG. 10). The mice treated with OX40L-PeptiCRAd showed significantly more MAGE-A3-specific CD8+ T cells among all CD8+ T cells of the PBMCs than mock treated mice, indicating that the PeptiCRAd-treatment was able to elicit peptide-specific response in humanized mice (FIG. 11).

An Adenovirus with a 5/3 Chimeric Capsid can be Complexed with NY-ESO-I and MAGE-A3 Peptides in Optimal Complexing Conditions The interactions between peptide coating and adenovirus particles (AdV) was studied using surface plasmon resonance (SPR) technique. The main aims were 1) to determine the binding dynamics of NY-ESO-1 and MAGE-A3 peptides with viruses in different media (sterile water and A195-media, a commonly used media for virus preparations), 2) to estimate how many peptide molecules one virus particle can bind in each media and 3) to assess the stability of the peptide-virus complexes. Peptide coatings were as follows PEP1455=KKKKKK-VFGIELMEVDPIGHLYIFAT (SEQ ID NO: 4); PEP1456=KKKKKKKKK-VFGIELMEVDPIGHLYIFAT (SEQ ID NO: 7); PEP1508=KKKKKK-YLAMPFATPMEAELARRSLA (SEQ ID NO: 5).

The SPR response for AdV particles in sterile water is ~0.7°, which corresponds to a 50% of viruses covering the detection area (1.4° corresponds to 100% coverage) (Table 10), giving an estimate that $5 \times 10^7$ virus particles are adsorbed within the detection area. When the AdV particles were run in A195 buffer, the SPR response was ~1.2°, which corresponds to a coverage of 86% of the detection surface (FIG. 12). These results give an estimate of $8.6 \times 10^7$ virus particles adsorbed within the detection area. These results may indicate that the structure of the viruses is preserved better in A195 buffer than in sterile water, or that A195 buffer facilitates the adsorption of viruses to the APTES surface.

Figure 12B:
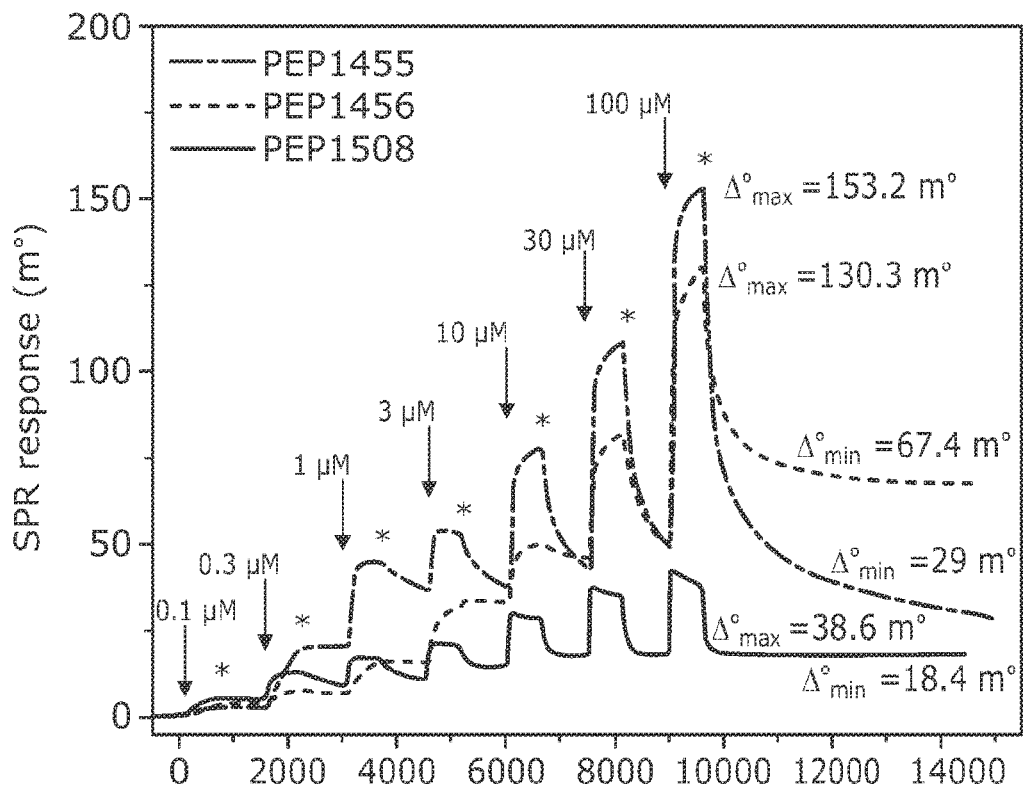

Peptides 1455 and 1508 seem to adsorb better on the immobilized virus particles in sterile water than in A195 media (FIGS. 12B and 13). The opposite is true for peptide 1456, which is adsorbed on the immobilized virus particles significantly better in the A195 buffer than in water. The number of peptides adsorbed per virus is calculated in Table 10.

Based on the results, PEP1455 was not completely soluble in A195 buffer and it seems that PEP1456 is a more potential modification in terms of solubility and coating efficiency, as judged by peptide to virus ratio in A195 buffer. Results indicate that peptide virus complexes can be prepared using an Adenovirus construct with a 5/3-chimeric capsid and 6/9K-peptides in an appropriate buffer environment. The complexes are quite stable without the free peptide environment as shown by SPR results. Further, the peptide to virus particle ratio is a peptide sequence-specific factor and also depends on the presence of optimal conditions for complex formation.

SUMMARY

With the three tested peptides, one 6K-MAGE-A3 and two 6K-NY-ESO-1, complex size seems to be dependent on peptide to virus ratio and seems to be a peptide specific property that has to be determined for each peptide and each combination of peptides and virus. Aggregation and possible non-specific interactions during complex formation can be prevented to some extent by preparing the complex in physiological salt solution instead of water in case of 6K-NY-ESO-1 (p91-110) but with 6K-NY-ESO-1 (p81-100) this was not the case, suggesting a peptide specific behavior.

The complex formation with 6K-MAGE-A3 peptide did not deteriorate infectivity of the virus significantly with 62% of infectivity remaining when using a relevant peptide to virus ratio.

Based on MAGE-A3 complex stability results the optimal storage conditions for the complex seems to be either +4° C. or −20° C.

PeptiCRAd with peptide coating(s) is superior to naked oncolytic adenovirus (VALO-C1) or standard peptide vaccination in triggering systemic tumor-targeted CD8+ T-cell responses and infiltration of CD8+ TILs into untreated distant tumors. The data suggest that PeptiCRAd improves the tumor targeting specificity of a standard oncolytic virus.

TABLE 1

Average diameter and zeta potential of peptide-virus-complexes prepared by mixing virus and peptide in proportions of 1E+9 virus particles with 20 or 40 μg of MAGE-A3-peptides with 6 or 9 lysine tail.

| Sample | Hydrodynamic diameter (nm) | Zeta Potential (mV) |
| --- | --- | --- |
| Ad5/3 + 6K-MAGE-A3, 20 μg | 181.1 | 30.3 |
| Ad5/3 + 6K-MAGE-A3, 40 μg | 178.9 | 34.2 |
| Ad5/3 + 6K-MAGE-A3, 20 μg 1.5 h | 222.3 | 28.2 |
| Ad5/3 + 6K-MAGE-A3, 40 μg 1.5 h | 185.6 | 31.1 |
| Ad5/3 + 9K-MAGE-A3, 20 μg | 200.5 | 20.7 |
| Ad5/3 + 9K-MAGE-A3, 40 μg | 197.4 | 24.0 |
| Ad5/3 + 9K-MAGE-A3, 20 μg 1.5 h | 212.0 | 28.6 |
| Ad5/3 + 9K-MAGE-A3, 40 μg 1.5 h | 310.9 | 30.4 |

TABLE 2

Average hydrodynamic diameter and zeta potential of peptide-virus-complexes measured immediately or after 2 hours from preparation by mixing 3E+9 virus particles with different amounts of 6K-MAGE-A3 peptide as indicated in the table.

| Sample | Z-Ave d. (nm) | ZP (mV) |
| --- | --- | --- |
| Ad5/3 virus only 15' | 125.3 | −19.6 |
| Ad5/3 virus only 2 h | 179.5 | −15.2 |
| Ad5/3 + 15 μg 6K-MAGE-A3 15' | 143.2 | 28.2 |
| Ad5/3 + 15 μg 6K-MAGE-A3 2 h | 160.9 | 28.4 |
| Ad5/3 + 30 μg 6K-MAGE-A3 15' | 172.4 | 31.3 |
| Ad5/3 + 30 μg 6K-MAGE-A3 2 h | 153.0 | 31.5 |
| Ad5/3 + 45 μg 6K-MAGE-A3 15' | 151.9 | 31.1 |
| Ad5/3 + 45 μg 6K-MAGE-A3 2 h | 201.6 | 34.9 |

TABLE 2-continued

Average hydrodynamic diameter and zeta potential of peptide-virus-complexes measured immediately or after 2 hours from preparation by mixing 3E+9 virus particles with different amounts of 6K-MAGE-A3 peptide as indicated in the table.

| Sample | Z-Ave d. (nm) | ZP (mV) |
| --- | --- | --- |
| Ad5/3 + 60 µg 6K-MAGE-A3 15' | 165.8 | 35.2 |
| Ad5/3 + 60 µg 6K-MAGE-A3 2 h | 207.5 | 54.1 |

TABLE 3

Average hydrodynamic diameter and zeta potential results of peptide-virus-complexes prepared by mixing 3E+9 virus particles with different amounts of 6K-MAGE-A3 peptide.

| Sample | Z-Ave d. (nm) | ZP (mV) |
| --- | --- | --- |
| Ad5/3 virus only in water | 125.3 | −19.5 |
| Ad5/3 + 0.1 µg 6K-MAGE-A3, 15' | 3078.7 | 0.4 |
| Ad5/3 + 0.5 µg 6K-MAGE-A3, 15' | 235.8 | 20.4 |
| Ad5/3 + 0.75 µg 6K-MAGE-A3, 15' | 262.6 | 20.2 |
| Ad5/3 + 1 µg 6K-MAGE-A3, 15' | 194.2 | 35.6 |
| Ad5/3 + 5 µg 6K-MAGE-A3, 15' | 186.2 | 23.4 |
| Ad5/3 + 10 µg 6K-MAGE-A3, 15' | 185.2 | 27.7 |
| Ad5/3 + 15 µg 6K-MAGE-A3, 15' | 164.6 | 30.3 |

TABLE 4

Infectivity of PeptiCRAd complexes prepared using different MAGE-A3-peptide to virus (3E+9 vp) ratios.

| Sample | Infectivity titer (ICC) |
| --- | --- |
| Ad5/3 virus only in water | 100% |
| +0.1 µg 6K-MAGE-A3 | 65% |
| +1.1 µg 6K-MAGE-A3 | 62% |
| +15 µg 6K-MAGE-A3 | 22% |

TABLE 5

Average hydrodynamic diameter and zeta potential results of peptide-virus-complexes prepared by mixing 3E+9 virus particles with 15 µg or 30 µg of 6K-MAGE-A3 peptide after keeping at different temperatures for 18-20 hours.

| Sample | Z-Ave d. (nm) | ZP (mV) | Average d. (nm) |
| --- | --- | --- | --- |
| Ad5/3 15 µg 6K-MAGE-A3, RT | 252.0 | 33.5 | |
| Ad5/3 30 µg 6K-MAGE-A3, RT | 226.8 | 33.4 | 239.4 |
| Ad5/3 15 µg 6K-MAGE-A3, +4° C. | 179.8 | 31.5 | |
| Ad5/3 30 µg 6K-MAGE-A3, +4° C. | 248.8 | 32.8 | 214.3 |
| Ad5/3 15 µg 6K-MAGE-A3, −20° C. | 152.6 | 33.0 | |
| Ad5/3 30 µg 6K-MAGE-A3, −20° C. | 177.8 | 36.0 | 165.2 |
| Ad5/3 15 µg 6K-MAGE-A3, −80° C. | 306.3 | 32.3 | |
| Ad5/3 30 µg 6K-MAGE-A3, −80° C. | 245.5 | 33.9 | 275.9 |

TABLE 6 a

Average hydrodynamic diameter and zeta potential of peptide-virus-complexes prepared by mixing 3E+9 virus particles with different amounts of 6K-NY-ESO-1 peptide (p81-100).

| Sample | Z-Ave d. (nm) | ZP (mV) |
| --- | --- | --- |
| Ad5/3 virus only in water | 132.5 | −26.6 |
| +0.1 µg 6K-NY-ESO-1 | 466.3 | −23.4 |
| +1 µg 6K-NY-ESO-1 | 594.9 | 1.8 |
| +15 µg 6K-NY-ESO-1 | 553.8 | 20.6 |
| +30 µg 6K-NY-ESO-1 | 265.1 | 24.9 |
| +60 µg 6K-NY-ESO-1 | 179.6 | 26.6 |
| +120 µg 6K-NY-ESO-1 | 344.4 | 31.9 |

TABLE 6 b

Average hydrodynamic diameter and zeta potential of peptide-virus-complexes prepared by mixing 3E+9 virus particles with different amounts of 6K-NY-ESO-1 peptide (p91-110).

| | Z-Ave d. (nm) | ZP (mV) |
| --- | --- | --- |
| Ad5/3 virus only in water | 169 | −18 |
| +0.1 µg 6K-NY-ESO-1 | 118 | −3 |
| +0.5 µg 6K-NY-ESO-1 | 205 | −1 |
| +1 µg 6K-NY-ESO-1 | 202 | 0 |
| +5 µg 6K-NY-ESO-1 | 1409 | 6 |
| +15 µg 6K-NY-ESO-1 | 1772 | 11 |
| +30 µg 6K-NY-ESO-1 | 3167 | 14 |
| +60 µg 6K-NY-ESO-1 | 2449 | 16 |
| +120 µg 6K-NY-ESO-1 | 2346 | 18 |

TABLE 7 a

Average hydrodynamic diameter and zeta potential of peptide-virus-complexes prepared by mixing 3E+9 virus particles with 1 µg of both 6K-NY-ESO-1-peptide (p81-100) and MAGE-A3-peptide either in water or in physiological NaCl (0.9%).

| Sample | Z-Ave d. (nm) | ZP (mV) |
| --- | --- | --- |
| Ad5/3 virus only in water | 132.9 | −25.0 |
| Ad5/3 + 1 ug 6K-MAGE-A3 + 1 ug 6K-NY-ESO-1 in water | 272.9 | 10.9 |
| Ad5/3 virus only in NaCl | 115.9 | −23.3 |
| Ad5/3 + 1 ug 6K-MAGE-A3 + 1 ug 6K-NY-ESO-1 in NaCl | 301.3 | 26.7 |

TABLE 7 b

Average hydrodynamic diameter and zeta potential of peptide-virus-complexes prepared by mixing 3E+9 virus particles with 1 µg of both 6K-NY-ESO-1-peptide (p91-110) and 6K-MAGE-A3-peptide either in water or in physiological NaCl (0.9%).

| Sample | Z-Ave d. (nm) | ZP (mV) |
| --- | --- | --- |
| Ad5/3 virus only in water | 132.9 | −25.0 |
| Ad5/3 + 1 µg MAGE-A3 + 1 µg NY-ESO-1 in water | 487.2 | 19.7 |
| Ad5/3 virus only in NaCl | 115.9 | −23.3 |
| Ad5/3 + 1 µg MAGE-A3 + 1 µg NY-ESO-1 in NaCl | 383.5 | 27.2 |

TABLE 8 a

Average hydrodynamic diameter and zeta potential of peptide-virus-complexes prepared by mixing 3E+9 virus particles with different amounts of 6K-NY-ESO-1 peptide (p81-100) in physiological NaCl (0.9%).

| Sample | Z-Ave d. (nm) | ZP (mV) |
| --- | --- | --- |
| Ad5/3 virus only in water | 198.8 | −25.5 |
| Ad5/3 virus only in NaCl | 128.1 | −22.2 |
| +0.1 µg | 132.3 | −22.2 |

TABLE 8 a-continued

Average hydrodynamic diameter and zeta potential of peptide-virus-complexes prepared by mixing 3E+9 virus particles with different amounts of 6K-NY-ESO-1 peptide (p81-100) in physiological NaCl (0.9%).

| Sample | Z-Ave d. (nm) | ZP (mV) |
|---|---|---|
| +1 μg | 2149.0 | 0.1 |
| +5 μg | 350.4 | 16.3 |
| +15 μg | 419.7 | 22.5 |
| +30 μg | 471.2 | 23.5 |
| +60 μg | 464.6 | 26.1 |
| +120 μg | 832.8 | 29.3 |

TABLE 8 b

Average hydrodynamic diameter and zeta potential of peptide-virus-complexes prepared by mixing 3E+9 virus particles with different amounts of 6K-NY-ESO-1 peptide (p91-110) in physiological NaCl (0.9%).

| Sample | Z-Ave d. (nm) | ZP (mV) |
|---|---|---|
| Ad5/3 virus only in water | 129.8 | −20.9 |
| Ad5/3 virus only in NaCl | 203.5 | −19.5 |
| +0.1 μg | 211.7 | −13.7 |
| +1 μg | 217.2 | −2.0 |
| +5 μg | 244.9 | 1.1 |
| +15 μg | 337.4 | 5.7 |
| +30 μg | 401.2 | 4.9 |
| +60 μg | 373.4 | 4.7 |
| +120 μg | 239.0 | 4.2 |

Table 9. The animals treated with PeptiCRAd showed more CD8+ and CD4+ T-cells in untreated distant tumors than in treated primary tumors, suggesting that the PeptiCRAd treatment enables more efficient antigen presentation and subsequent T cell homing to distant tumors compared to OV. Results are depicted as ratio of the number of tumor infiltrating lymphocytes in untreated to treated tumors ±SEM.

TABLE 9

The animals treated with PeptiCRAd showed more CD8+ and CD4+ T-cells in untreated distant tumors than in treated primary tumors, suggesting that the PeptiCRAd treatment enables more efficient antigen presentation and subsequent T cell homing to distant tumors compared to OV. Results are depicted as ratio of the number of tumor infiltrating lymphocytes in untreated to treated tumors ± SEM.

| Tumor infiltrating lymphocytes | RATIO (untreated:treated) | | |
|---|---|---|---|
| | Peptide vaccine (0.12 + 30 ug)* N = 5-6 | OV ($10^8$ VP) N = 5 | PeptiCRAs ($10^7 + 10^8$) N = 17-20 |
| Total human lymphocytes (CD45) | 1.3 ± 0.3 | 0.7 ± 0.1 | 1.8 ± 0.5 |
| Total human T cells (CD3) | 1.4 ± 0.3 | 0.6 ± 0.1 | 1.7 ± 0.5 |
| CD8+ T-cells | 0.8 ± 0.3 | 0.6 ± 0.1 | 1.6 ± 0.6 |
| CD4+ T-cells | 0.9 ± 0.3 | 0.5 ± 0.1 | 1.7 ± 0.6 |

TABLE 10

The results based on the SPR measurements for virus and virus-peptide -complex.

| Interaction media | Adsorbed virus SPR response (Δ°) | Radius (nm) | Number of viruses on sensor surface | Peptide | Adsorbed Peptides SPR response (Δ°) | Mass/ Area Peptide (ng/cm²) | Mass Peptide (ng) | $M_w$ Peptide (g/mol) | Moles peptide (mol) | Number of peptides adsorbed | Number of Peptides adsorbed/ virus particle |
|---|---|---|---|---|---|---|---|---|---|---|---|
| Min | | | | | | | | | | | |
| Water | 0.7 | 100 | 49999841 | PEP1455 | 0.0674 | 40.44 | 0.32 | 3033.7 | 1.04708E−13 | 6.30549E+10 | 1261 |
| Water | 0.7 | 100 | 49999841 | PEP1456 | 0.029 | 17.4 | 0.14 | 3418.3 | 3.99833E−14 | 2.40779E+10 | 482 |
| Water | 0.7 | 100 | 49999841 | PEP1508 | 0.0184 | 11.04 | 0.09 | 3007.7 | 2.88319E−14 | 1.73626E+10 | 347 |
| Max | | | | | | | | | | | |
| Water | 0.7 | 100 | 49999841 | PEP1455 | 0.1532 | 91.92 | 0.72 | 3033.7 | 2.38E−13 | 1.43324E+11 | 2866 |
| Water | 0.7 | 100 | 49999841 | PEP1456 | 0.1303 | 78.18 | 0.61 | 3418.3 | 1.79649E−13 | 1.08185E+11 | 2164 |
| Water | 0.7 | 100 | 49999841 | PEP1508 | 0.0386 | 23.16 | 0.18 | 3007.7 | 6.04844E−14 | 3.64237E+10 | 728 |
| Min | | | | | | | | | | | |
| A195 | 1.2 | 100 | 85714013 | PEP1455 | 0.0174 | 10.44 | 0.08 | 3033.7 | 2.70313E−14 | 1.62783E+10 | 190 |
| A195 | 1.2 | 100 | 85714013 | PEP1456 | 0.2762 | 165.72 | 1.30 | 3418.3 | 3.80806E−13 | 2.29322E+11 | 2675 |
| A195 | 1.2 | 100 | 85714013 | PEP1508 | 0.012 | 7.2 | 0.06 | 3007.7 | 1.88034E−14 | 1.13234E+10 | 132 |
| Max | | | | | | | | | | | |
| A195 | 1.2 | 100 | 85714013 | PEP1455 | 0.078 | 46.8 | 0.37 | 3033.7 | 1.21175E−13 | 72971496170 | 851 |
| A195 | 1.2 | 100 | 85714013 | PEP1456 | 0.3712 | 222.72 | 1.75 | 3418.3 | 5.11786E−13 | 3.08197E+11 | 3596 |
| A195 | 1.2 | 100 | 85714013 | PEP1508 | 0.044 | 26.4 | 0.21 | 3007.7 | 6.89459E−14 | 4.15192E+10 | 484 |

The invention claimed is:

1. A modified adenovirus comprising:
   at least one polypeptide attached covalently or non-covalently onto the viral capsid without having been genetically encoded by said adenovirus, wherein the at least one polypeptide comprises:
   i) VFGIELMEVDPIGHLYIFAT [SEQ ID NO:1];
   ii) YLAMPFATPMEAELARRSLA [SEQ ID NO:2]; or
   iii) a polypeptide that is at least 90% identical to SEQ ID NO: 1 or SEQ ID NO: 2;
   a deletion of the 14.7 k gene;
   a transgene encoding CD40L; and
   a transgene encoding OX40L situated in the E3 region of the modified adenovirus.

2. The modified adenovirus according to claim 1 wherein said at least one polypeptide further comprises at least 3, 4, 5, 6, 7, 8, or 9 lysines.

3. The modified adenovirus according to claim 2 wherein said lysines are attached at the amino end of the at least one polypeptide.

4. The modified adenovirus according to claim 1 wherein said at least one polypeptide comprises:
   KKKKKK(KKK)-VFGIELMEVDPIGHLYIFAT [SEQ ID NO:7]; and/or
   KKKKKK(KKK)-YLAMPFATPMEAELARRSLA [SEQ ID NO:8]; alternatively:
   KKKKKK-VFGIELMEVDPIGHLYIFAT [SEQ ID NO:4]; and/or
   KKKKKK-YLAMPFATPMEAELARRSLA [SEQ ID NO:5].

5. The modified adenovirus according to claim 1 wherein said adenovirus is a human adenovirus.

6. The modified adenovirus according to claim 1 wherein said adenovirus further comprises modifications in E1 and/or E4 and/or L3 genes.

7. The modified adenovirus according to claim 1 wherein said adenovirus is further modified to include an Ad5/3 chimeric substitution, wherein the serotype 5 adenoviral fiber knob region is replaced with a serotype 3 adenovirus fiber knob region.

8. The modified adenovirus according to claim 1 wherein said adenovirus is further modified to include a E1A gene deletion wherein the deletion is of at least those nucleotides encoding amino acids 122-129.

9. The modified adenovirus according to claim 1, wherein said transgenes are human.

10. The modified adenovirus according to claim 1 wherein the polypeptide to virus ratio is in the range from 1 to 5 μg per 3E+9 Virus Particles.

11. A pharmaceutical composition comprising at least one modified adenovirus according to claim 1 in combination with a suitable carrier.

12. The pharmaceutical composition according to claim 11 wherein said composition is formulated for intratumoral, intramuscular, intra-arterial, intravenous, intrapleural, intravesicular, intradermal, intracavitary or peritoneal injection, or an oral administration.

13. A method of treating cancer in a patient comprising administering to a patient an effective amount of at least one adenovirus according to claim 1.

14. The method of treating cancer according to claim 13 wherein the at least one adenovirus is administered with a cell checkpoint modulator.

15. The method of treating cancer according to claim 14 wherein the checkpoint modulator is an anti-PD1 molecule, an anti-PD-L1 molecule or an anti-CTLA-4 molecule.

16. The method according to claim 13 wherein said cancer includes any one or more of the following cancers: nasopharyngeal cancer, synovial cancer, hepatocellular cancer, renal cancer, cancer of connective tissues, melanoma, lung cancer, bowel cancer, colon cancer, rectal cancer, brain cancer, throat cancer, oral cancer, liver cancer, bone cancer, pancreatic cancer, choriocarcinoma, gastrinoma, pheochromocytoma, prolactinoma, T-cell leukemia/lymphoma, neuroma, von Hippel-Lindau disease, Zollinger-Ellison syndrome, adrenal cancer, anal cancer, bile duct cancer, bladder cancer, ureter cancer, oligodendroglioma, neuroblastoma, meningioma, spinal cord tumor, osteochondroma, chondrosarcoma, Ewing's sarcoma, cancer of unknown primary site, carcinoid, carcinoid of gastrointestinal tract, fibrosarcoma, breast cancer, Paget's disease, cervical cancer, esophagus cancer, gall bladder cancer, head cancer, eye cancer, neck cancer, kidney cancer, Wilms' tumor, Kaposi's sarcoma, prostate cancer, testicular cancer, Hodgkin's disease, non-Hodgkin's lymphoma, skin cancer, mesothelioma, multiple myeloma, ovarian cancer, endocrine pancreatic cancer, glucagonoma, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, acoustic neuroma, mycosis fungoides, insulinoma, carcinoid syndrome, somatostatinoma, gum cancer, heart cancer, lip cancer, meninges cancer, mouth cancer, nerve cancer, palate cancer, parotid gland cancer, peritoneum cancer, pharynx cancer, pleural cancer, salivary gland cancer, tongue cancer and tonsil cancer.

17. The modified adenovirus according to claim 1, wherein the CD40L transgene is inserted immediately downstream from the OX40L transgene using a 2A processing site.

18. The modified adenovirus according to claim 1, wherein said adenovirus is a serotype 5 adenovirus.

19. The modified adenovirus according to claim 5, wherein said human adenovirus is a serotype 5 adenovirus.

20. The modified adenovirus according to claim 6, wherein the modifications in the E1 and/or E4 and/or L3 genes comprise insertion of tumour specific promoters.

* * * * *

SEQUENCE LISTING

<160> NUMBER OF SEQ ID NOS: 9

<210> SEQ ID NO 1
<211> LENGTH: 20
<212> TYPE: PRT

<213> ORGANISM: Homo sapiens

<400> SEQUENCE: 1

Val Phe Gly Ile Glu Leu Met Glu Val Asp Pro Ile Gly His Leu Tyr
1               5                   10                  15

Ile Phe Ala Thr
            20

<210> SEQ ID NO 2
<211> LENGTH: 20
<212> TYPE: PRT
<213> ORGANISM: Homo sapiens

<400> SEQUENCE: 2

Tyr Leu Ala Met Pro Phe Ala Thr Pro Met Glu Ala Glu Leu Ala Arg
1               5                   10                  15

Arg Ser Leu Ala
            20

<210> SEQ ID NO 3
<211> LENGTH: 20
<212> TYPE: PRT
<213> ORGANISM: Homo sapiens

<400> SEQUENCE: 3

Arg Gly Pro Glu Ser Arg Leu Leu Glu Phe Tyr Leu Ala Met Pro Phe
1               5                   10                  15

Ala Thr Pro Met
            20

<210> SEQ ID NO 4
<211> LENGTH: 26
<212> TYPE: PRT
<213> ORGANISM: Homo sapiens

<400> SEQUENCE: 4

Lys Lys Lys Lys Lys Lys Val Phe Gly Ile Glu Leu Met Glu Val Asp
1               5                   10                  15

Pro Ile Gly His Leu Tyr Ile Phe Ala Thr
            20                  25

<210> SEQ ID NO 5
<211> LENGTH: 26
<212> TYPE: PRT
<213> ORGANISM: Homo sapiens

<400> SEQUENCE: 5

Lys Lys Lys Lys Lys Lys Tyr Leu Ala Met Pro Phe Ala Thr Pro Met
1               5                   10                  15

Glu Ala Glu Leu Ala Arg Arg Ser Leu Ala
            20                  25

<210> SEQ ID NO 6
<211> LENGTH: 26
<212> TYPE: PRT
<213> ORGANISM: Homo sapiens

<400> SEQUENCE: 6

Lys Lys Lys Lys Lys Lys Arg Gly Pro Glu Ser Arg Leu Leu Glu Phe
1               5                   10                  15

Tyr Leu Ala Met Pro Phe Ala Thr Pro Met
            20                  25

```
<210> SEQ ID NO 7
<211> LENGTH: 29
<212> TYPE: PRT
<213> ORGANISM: Homo sapiens

<400> SEQUENCE: 7

Lys Lys Lys Lys Lys Lys Lys Lys Lys Val Phe Gly Ile Glu Leu Met
1               5                   10                  15

Glu Val Asp Pro Ile Gly His Leu Tyr Ile Phe Ala Thr
            20                  25

<210> SEQ ID NO 8
<211> LENGTH: 29
<212> TYPE: PRT
<213> ORGANISM: Homo sapiens

<400> SEQUENCE: 8

Lys Lys Lys Lys Lys Lys Lys Lys Lys Tyr Leu Ala Met Pro Phe Ala
1               5                   10                  15

Thr Pro Met Glu Ala Glu Leu Ala Arg Arg Ser Leu Ala
            20                  25

<210> SEQ ID NO 9
<211> LENGTH: 29
<212> TYPE: PRT
<213> ORGANISM: Homo sapiens

<400> SEQUENCE: 9

Lys Lys Lys Lys Lys Lys Lys Lys Lys Arg Gly Pro Glu Ser Arg Leu
1               5                   10                  15

Leu Glu Phe Tyr Leu Ala Met Pro Phe Ala Thr Pro Met
            20                  25
```